United States Patent [19]
Walters

[11] Patent Number: 6,078,490
[45] Date of Patent: Jun. 20, 2000

[54] METHOD OF TREATING MATERIALS WITH PULSED ELECTRICAL FIELDS

[75] Inventor: Richard E. Walters, Columbia, Md.

[73] Assignee: Cyto Pulse Sciences, Inc., Hanover, Md.

[21] Appl. No.: 09/313,260

[22] Filed: May 18, 1999

Related U.S. Application Data

[63] Continuation of application No. 08/569,664, Dec. 8, 1995.

[51] Int. Cl.⁷ ...................................................... H02H 3/14
[52] U.S. Cl. .............................................. 361/88; 323/220
[58] Field of Search .................................... 323/220, 222, 323/233, 281, 282, 284; 307/18, 19, 20, 21, 24, 28, 31, 33, 39, 46, 85, 86, 87, 109, 110; 361/17, 18, 86, 88, 91.2, 21, 33

[56] References Cited

U.S. PATENT DOCUMENTS 4,459,541  7/1984  Fielden et al. ..................... 324/60 CD
5,444,358  8/1995  Delepaut ................................ 323/222

*Primary Examiner*—Ronald W. Leja
*Attorney, Agent, or Firm*—Marvin S. Towsend; James H. Laughlin, Jr.

[57] ABSTRACT

A method is provided for treating materials, especially organic materials, with pulsed electrical fields, wherein the method includes the step of applying an agile pulse sequence having at least three pulses to a material, wherein the agile pulse sequence has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. When biological cells are treated to form pores in an electroporation procedure, the induced pores are sustained for a relatively long period of time, and viability of the biological cells is maintained.

1 Claim, 15 Drawing Sheets

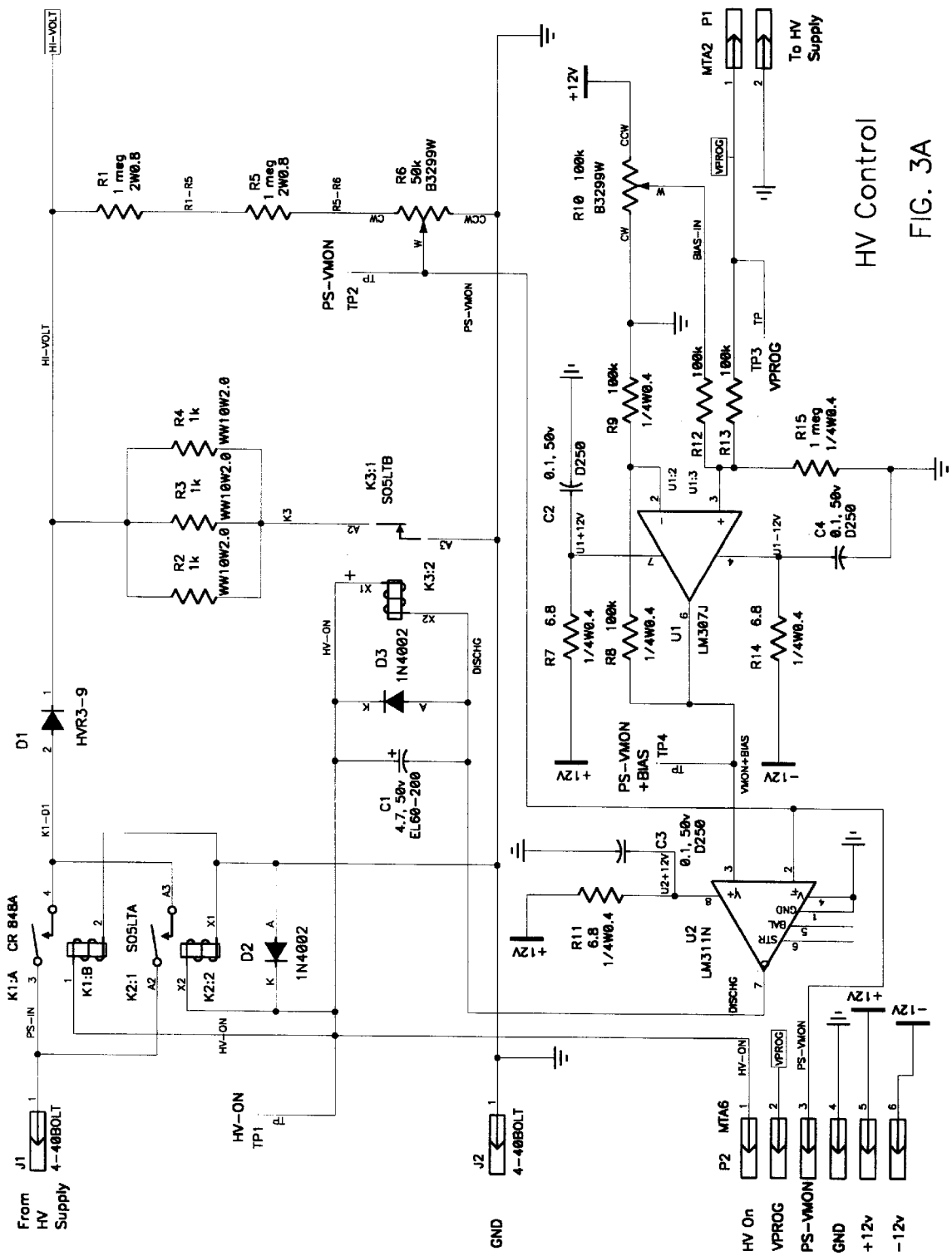
FIG. 3A HV Control

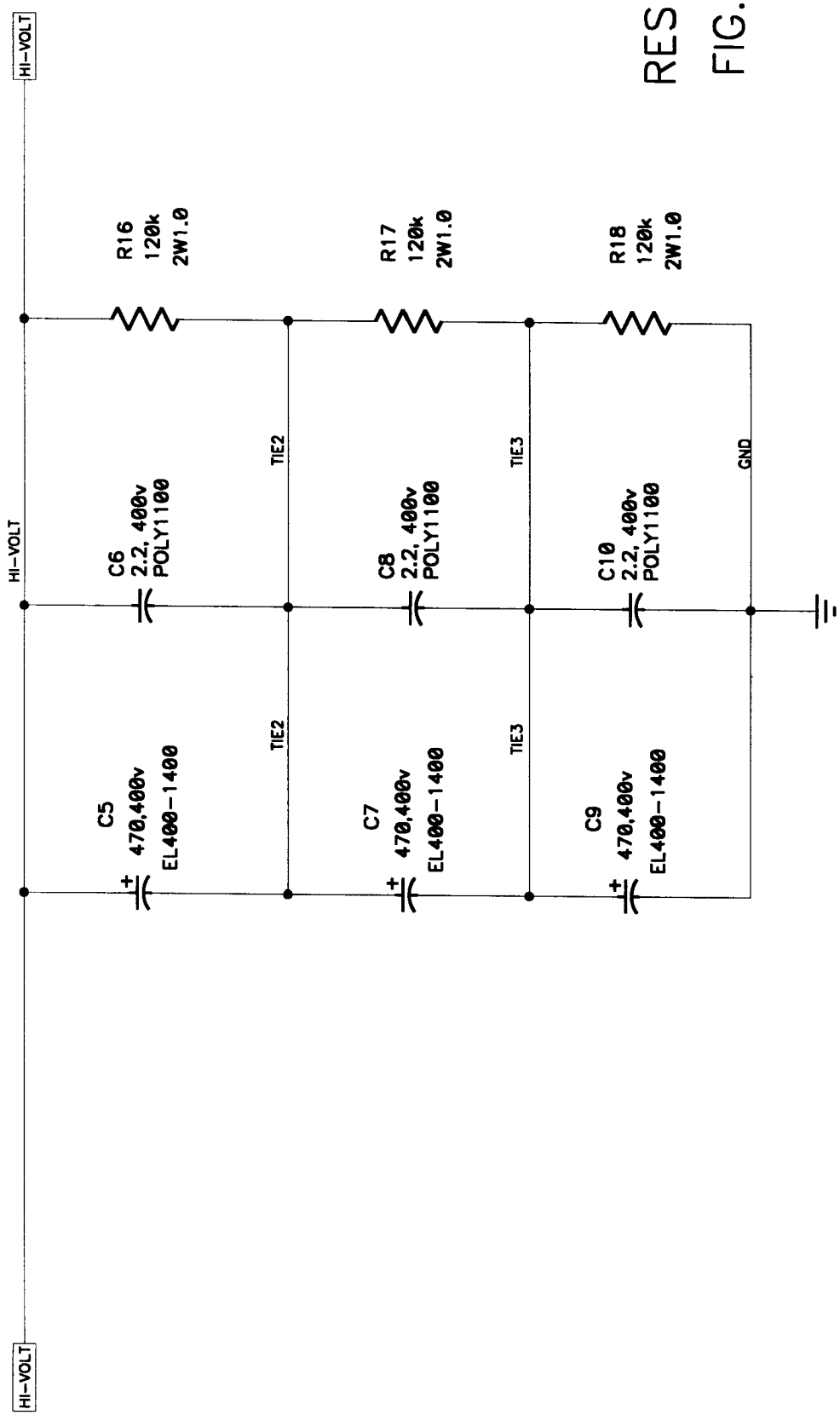

HV Switch

Pulse Monitors

Control

DAC

Pulse Gen Connect and Power Supply

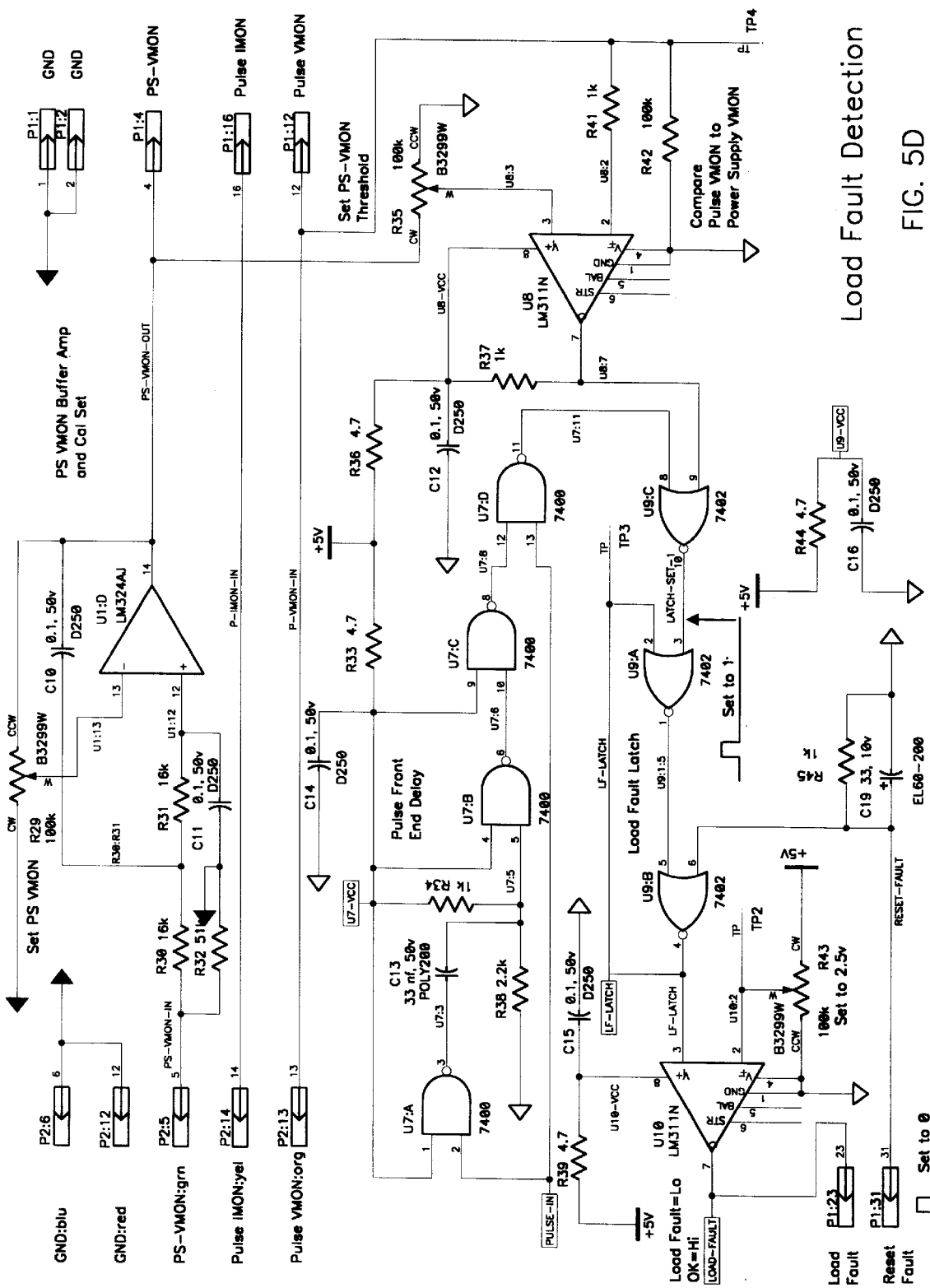
FIG. 5D  Load Fault Detection

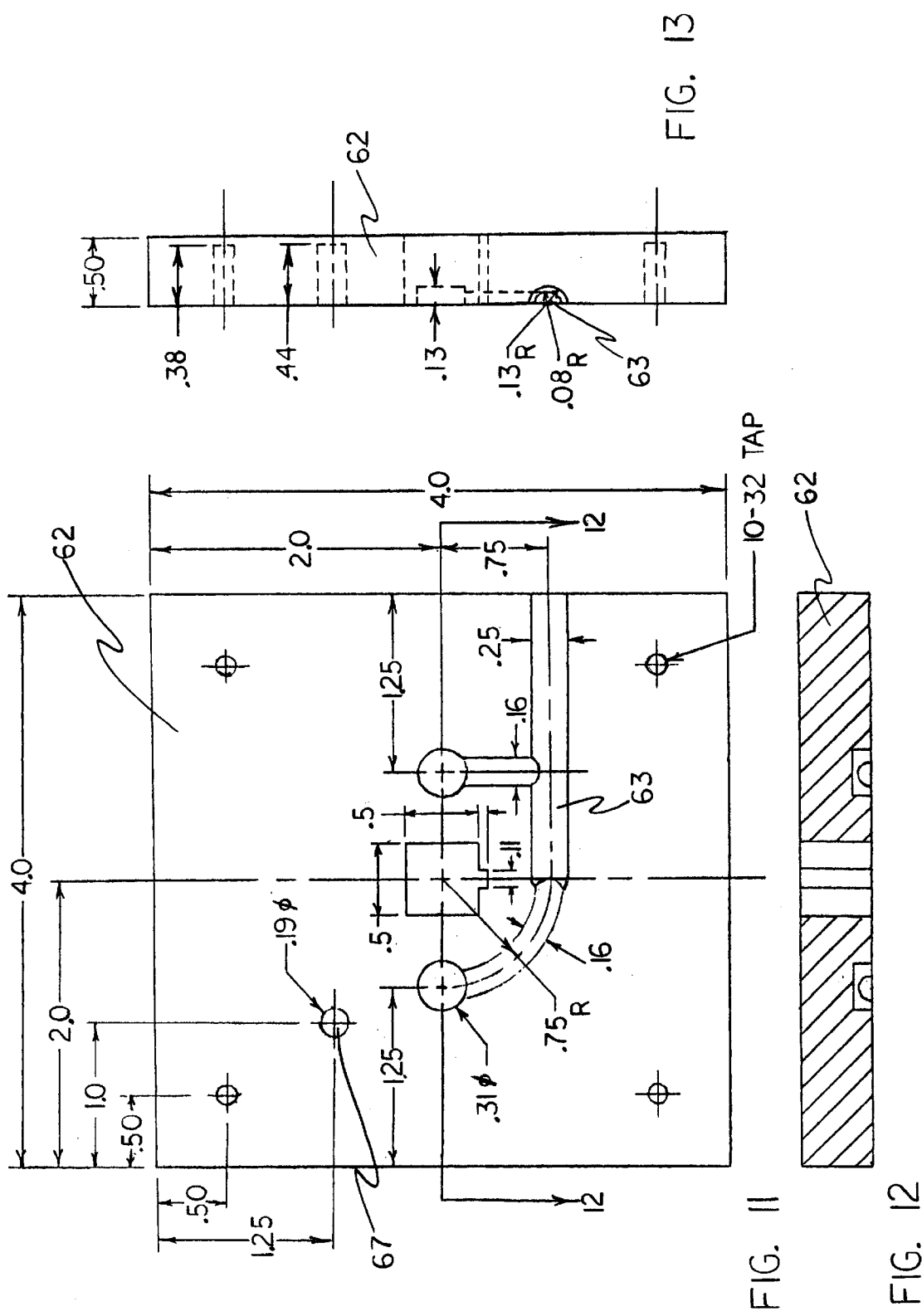

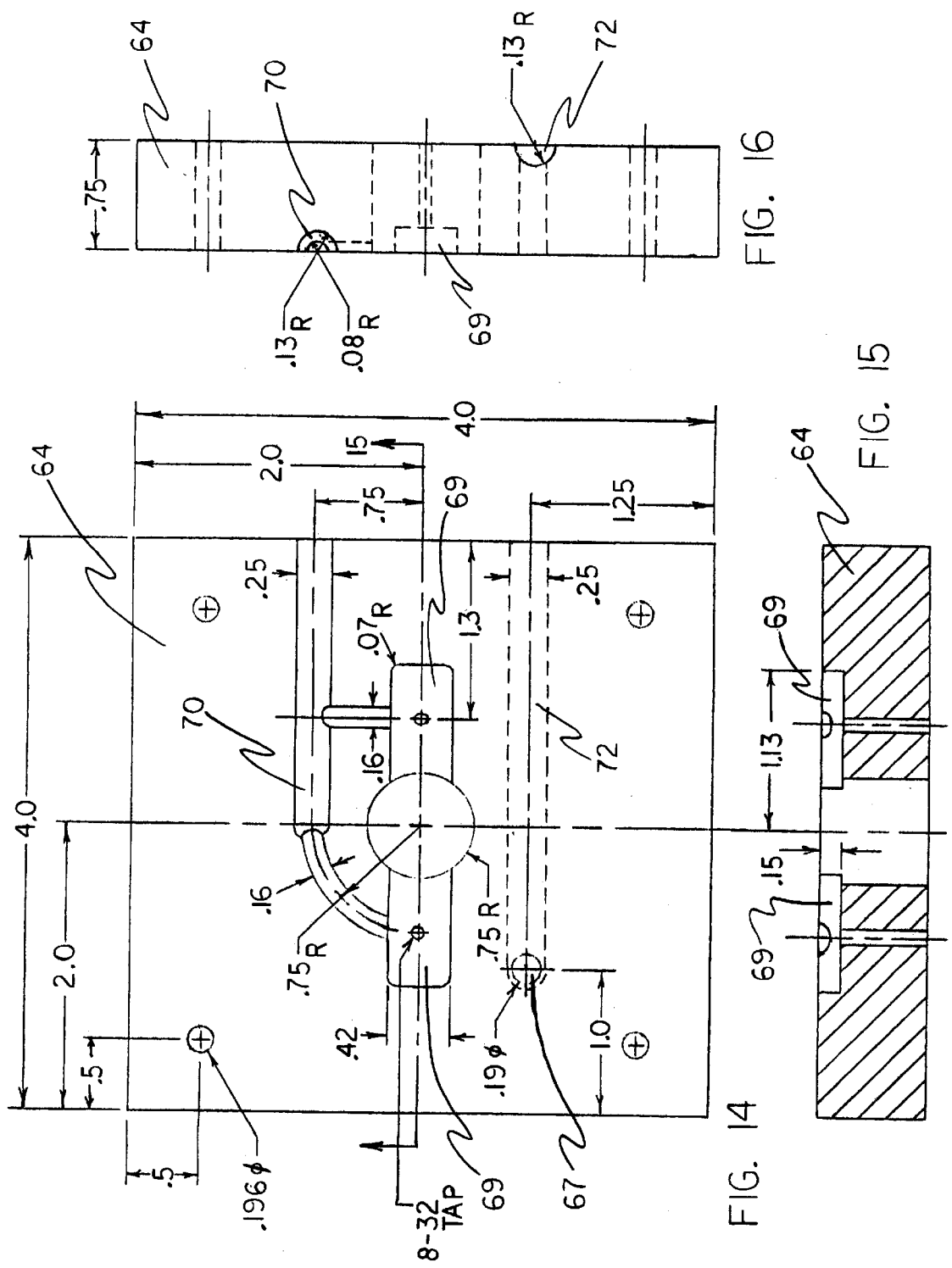

METHOD OF TREATING MATERIALS WITH PULSED ELECTRICAL FIELDS

This application is a continuation of application Ser. No. 08/569,664 filed Dec. 8, 1995.

FIELD OF INVENTION

This invention relates to a method of applying a defined pattern of pulsed electrical fields to materials, especially living cells. The method of the invention is especially applicable in the fields of electroporation, electrofusion, and electromanipulation.

BACKGROUND OF THE INVENTION

Electroporation and electrofusion are related phenomena with a variety of uses in manipulation of prokaryotic and eukaryotic cells. Electroporation is the destabalization of cell membranes by application of a brief electric potential (pulse) across the cell membrane. Properly administered, the destabalization results in a temporary pore in the membrane through which macromolecules can pass while the pore exists. Electrofusion is the fusion of two or more cells by application of a brief electric potential across a cell membrane. The physical and biological parameters of electrofusion are similar to those of electroporation.

The potential applied to cell membranes is applied using instruments delivering various pulse shapes. The two most common pulse shapes are exponential decay and rectangular wave. The exponential decay pulse is generated with capacitance discharge pulse generators. It is the least expensive pulse generator and gives the operator the least control over pulse parameters. The rectangular wave pulse generator is more expensive, gives more control over pulse parameters and generates a pulse that is less lethal to cells. With both pulse shapes, the energy needed to generate resealable pores in cells is related to cell size, shape, and composition.

With electrofusion, cells must be in contact at the time of membrane destabalization. This is accomplished by physical means such as centrifugation, biochemical means such as antibody bridging, or electrical means through dielectrophoresis. Dielectrophoresis is the creation of a dipole within a cell by application of a low voltage potential across a cell membrane in an uneven electrical field. The dipole can be created in Unipolar or AC fields. Since Unipolar fields tend to generate unacceptable heat, radio frequency AC is often used for dielectrophoresis.

The uses of electroporation and electrofusion are many. A partial list follows: (1) transient introduction of DNA or RNA into both eukaryotic and prokaryotic cells; (2) permanent transfection of DNA into both eukaryotic and prokaryotic cells; (3) permanent and temporary transfection of DNA into human and animal cells for gene therapy; (4) introduction of antibodies, other proteins, or drugs into cells; (5) production of antibody producing hybridomas; (6) pollen electrotransformation in plants; (7) electroinsertion; (8) manipulation of animal embryos; (9) electrofusion of adherent cells; (10) production of plant somatic hybrids; (11) DNA vaccination; and (12) cancer therapy.

One of the ways that electroporation or electrofusion works is to induce the formation of holes or pores in the cell membrane. There is some controversy about the exact nature of the cell pore induced by the application of an electrical pulse to a cell, but the practical effect is an induced cell permeability and a tendency to fuse with other similarly affected cells that are in close contact.

There is a Unipolar voltage threshold for the induction of pores in or for the fusion of cell membranes. Voltages below the threshold will not bring about substantial cell membrane disturbance. The threshold potential for many cells is approximately one volt across the cell membrane. The total voltage applied per centimeter between electrodes to achieve one volt potential across the cell membrane is therefore proportional to the diameter of a cell. Small cells such as bacteria, require high voltages while larger cells, such as many mammalian cells, require somewhat lower voltages. There are other cell specific variables such as the structure of the cellular cytoskeleton that affect the voltage required for that cell.

When using electrical pulses which are powerful enough to bring about electroporation or electrofusion of cells, the main problem is that the process is often lethal to an unacceptable percentage of the cells. The lethality rate may be 50% or higher. There are a number of reasons why such high lethality rates to cells are not desirable. When cells are treated for further use in ex vivo gene therapy, lethality to the cells will prevent an adequate number of cells from uptaking therapeutic genetic material. When in vivo gene therapy is employed in a patient, lethality to cells may not only result in less effective treatment, but may also result in injury to the patient.

A number of methods have been used to reduce cell killing in electroporation and electrofusion. The most commonly used method is to apply a rectangular shaped pulse to cells instead of an exponential decay pulse. This method reduces the total energy applied to the cell while applying enough voltage to overcome the threshold. While the rectangular shaped pulse is an improvement, there is still substantial cell killing during an effective application of electrical energy to the cells.

Rectangular wave pulsers currently marketed for electroporation and electrofusion have a number of adjustable parameters (voltage, pulse width, total number of pulses, and pulse frequency). These parameters, once set, are fixed for each pulse in each pulse session. For example if a voltage of 1,000 volts per centimeter, pulse width of 20 microseconds, pulse number equal to 10, and a pulse frequency of 1 Hz is chosen, then each of the 10 pulses will be fixed at 1000 volts per centimeter and 20 microseconds for the pulse session.

However, even when using rectangular wave pulsers that employ fixed pulse parameters, an undesirably high lethality rate of the cells may still occur. In this respect, it would be desirable if wave pulses could be controlled in such a way that the lethality rate of cells would be significantly reduced.

In an article by Sukharev et al entitled "Electroporation and electrophoretic DNA transfer into cells" in Biophys. J., Volume 63, November 1992, pages 1320–1327, there is a disclosure that two generators are employed to generate pulses. A time delay switch controls a first pulse generator to generate a first pulse to be imposed on biological Cos-1 cells. The first pulse has an amplitude sufficient to induce pore formation in the cells. The time delay switch causes a time delay and then controls a second pulse generator to generate a second pulse which is imposed on the cells. The second pulse is insufficient to sustain the induced pores formed from the first pulse. However, the second pulse is sufficient to bring about electrophoresis of DNA material into the previously pulsed cells. Several key points are noted with respect to the disclosures in the Sukharev et al article. First, the induced pores that are formed in the cells as a result of the first pulse begin to contract after the first pulse is over without any additional pulse being imposed on the cells sufficient to sustain the induced pores. Second, the Sukharev et al article does not address the issue of cell viability after the induced-pore-forming pulse. Third, there are only two pulses provided with Sukharev et al. Therefore, the time period that the DNA material can enter the cells is constrained by the effects of only two brief pulses. In this respect, it would be desirable if a pulse protocol were provided that sustains induced pores formed in electroporation. Moreover, it would be desirable if a pulse protocol were provided which is directed towards improving cell viability in cells undergoing electroporation. Furthermore, it would be desirable if a pulse protocol were provided which provides three or more pulses to allow more time for materials to enter cells undergoing electroporation.

In an article by Ohno-Shosaku et al entitled "Somatic Hybridization between Human and Mouse Lymphoblast Cells Produced by an Electric Pulse-Induced Fusion Technique" in Cell Structure and Function, Vol. 9, (1984), pages 193–196, there is a disclosure of the use of an alternating electric field of 0.8 kV/cm at 100 kHz to fuse biological cells together. It is noted that the alternating current provides a series of electrical pulses all of which have the same duration, the same magnitude, and the same interval between pulses.

In an article by Okamoto et al entitled "Optimization of Electroporation for Transfection of Human Fibroblast Cell Lines with Origin-Defective SV40 DNA: Development of Human Transformed Fibroblast Cell Lines with Mucopolysaccharidoses (I–VII)" in Cell Structure and Function, Vol.17, (1992), pages 123–128, there is a disclosure that a variety of electric parameters were tested to obtain optimum electroporation. The electric parameters included voltage, pulse-duration, the number of pulses, and pulse shape. It is noted that for any particular set of electric parameters that were selected, all of pulses with the selected parameters had the same duration, the same magnitude, and the same interval between pulses.

In an article by Orias et al entitled "Replacement of the macronuclear ribosomal RNA genes of a mutant Tetrahymena using electroporation" in Gene, Vol. 70, (1988), pages 295–301, there is a disclosure that two different electroporation devices were employed. It is noted that each electroporation device provided a series of electrical pulses (pulse train) for each electroporation run. For any particular electroporation run, all of the pulses in the pulse train had the same duration, the same magnitude, and the same interval between pulses.

In an article by Miller et al entitled "High-voltage electroporation of bacteria: Genetic transformation of Campylobacter jejuni with plasmid DNA" in Proc. Natl. Acad. Sci USA, Vol. 85, February 1988, pages 856–860, there is a disclosure that a variety of electric pulse parameters were tested to obtain optimum electroporation. The electric pulse parameters included field strength and time constant. It is noted that for any particular set of pulse parameters that were selected, all of pulses with the selected parameters had the same field strength and the same time constant.

In an article by Ogura et al entitled "Birth of normal young after electrofusion of mouse oocytes with round spermatids" in Proc. Natl. Acad. Sci USA, Vol. 91, August 1994, pages 7460–7462, there is a disclosure that oocytes were electroactivated by exposures to AC (2MHz, 20–50 V/cm for 10 seconds) and Rectangular (1500 V/cm for 80 microsec.) pulses in Dulbecco's PBS medium. Following electroactivation, the cells were removed from the Dulbecco's PBS medium and placed in a Hepes/Whitten medium and injected with single spermatids. The oocyte-spermatid pairs were placed in fusion medium and exposed to, in sequence, an AC pulse (2MHz, 100V/cm, for 15–30 seconds), a fusion Rectangular pulse (3750–4000 V/cm for 10 microsec.), and a subsequent AC pulse (2 MHz, 100V/cm for 15–30 seconds). The time interval between application of the oocyte activation pulse and the oocyte-spermatid fusion pulse was 15–40 minutes. Several points are noted with respect to the disclosures in the Ogura et al article. First, electroporation is not conducted; instead, electrofusion is conducted. Moreover, entry of the spermatid into the oocyte is by injection, not electroporation. Second, only two Rectangular pulses are employed. Neither of the AC pulses has a sufficient voltage level to provide an electroporation threshold. The sequence of two Rectangular pulses are not disclosed as having induced pore formation. Pore formation is not utilized in this method of cell fusion. No provision is made to sustain pores formed or to maintain viability of cells treated.

In an article by Andreason et al entitled "Optimization of electroporation for transfection of mammalian cell lines" in Anal. Biochem., Vol.180, No.2, pages 269–275, Aug. 1,1989, there is a disclosure that transfection by electroporation using square wave pulses, as opposed to exponentially decaying pulses, was found to be significantly increased by repetitive pulses. Different pulse amplitudes were tried in different experimental runs to determine the effects of different electric field strengths. For a given experimental run, each pulse has the same voltage and same duration as each other pulse.

In an article by Vanbever et al entitled "Transdermal Delivery of Metoprolol by Electroporation" in Pharmaceutical Research, Vol. 11, No. 11, pages 1657–1662, (1994), there is a disclosure that electroporation can be used to deliver drugs across skin tissues. The article discloses a series of electroporation experiments for the purpose of determining optimum electroporation conditions. An electroporation apparatus was employed that coud be programmed to produce three types of pulses based on exponentially decaying capacitive discharge: a single HV pulse (ranging from 3500V to 100V; a single LV pulse (ranging from 450V to 20V); and a twin pulse consisting of a first HV pulse, and interpulse delay (1 second), and a second LV pulse. If more than one pulse were applied, they were separated by 1 minute. It is noted that none of the pulses applied are rectangular in shape. In actual experiments run, using a twin pulse, the second LV pulse had a pulse amplitude of 100 volts (see FIGS. 1 and 2 on page 1659). As a result of comparisons made between the results of actual experiments conducted, it was concluded in the second column on page 1659 that "single pulse was as efficient as the twin pulse to promote metoprolol permeation, indicating that twin pulse application was not necessary". Moreover, a further conclusion beginning in the same column of the same page and extending to the first column of page 1660 states "long pulse (621±39 ms) at a low voltage was much more efficient than a high voltage pulse with a short pulse time (3.1±0.1 ms) to promote metoprolol permeation". Beginning in the first paragraph of the first column on page 1660, the authors state "The short high voltage pulses used in this study hardly had any effect, while pulses of hundreds of volts and a few ms time constants were reported to have dramatic effect on transdermal permeation". Clearly, Vanbever et al teach away from using a pulse train having pulses of different amplitudes. Moreover, nothing in the Vanbever et al article relates to the issue of cell viability for cells undergoing electroporation.

In an abstract of an article by Bahnson et al entitled "Addition of serum to electroporated cells enhances survival and transfection efficiency" in Biochem. Biophys. Res. Commun., Vol. 171, No. 2, pages 752–757, Sep. 14, 1990, there is a disclosure that serum rapidly reseals the membranes of electroporated cells and that timely addition of serum following electroporation can improve cell survival and transfection efficiency. Rather than require the use of serum, it would be desirable if an electrical way were provided to improve cell survival and transfection efficiency.

In an abstract of an article by Knutson et al entitled "Electroporation: parameters affecting transfer of DNA into mammalian cells" in Anal. Biochem., Vol. 164, No. 1, pages 44–52, July 1987, there is a disclosure of an instrument which permits the high-voltage discharge waveform to be varied with respect to rise time, peak voltage, and fall time. Tests were done in which the mammalian cells were exposed to multiple voltage discharges, but the multiple exposures did not improve DNA transfer. It is noted that with the use of multiple pulses, each pulse has the same voltage and same duration as each other pulse.

In an abstract of an article by Kubiniec et al entitled "Effects of pulse length and pulse strength on transfection by electroporation" in Biotechniques, Vol. 8, No. 1, pages 16–20, January 1990, there is a disclosure that the relative importance of pulse field strength E and pulse length tau ½ (half decay time of an exponential decay pulse) were investigated for HeLa or HUT-78 cells. In the abstract, there is no disclosure of using a plurality of pulses for carrying out the electroporation.

Throughout the years a number of innovations have been developed in the fields of electroporation, electrofusion, dielectrophoresis, and the U.S. patents discussed below are representative of some of those innovations.

U.S. Pat. No. 4,441,972 discloses a device for electrofusion, cell sorting, and dielectrophoresis which includes specially designed electrodes which provide a non-uniform electrical field. The non-uniform electric fields are used for sorting cells. More specifically, at least one of the electrodes has a surface which includes a plurality of substantially concentric grooves. Because preparation of such concentric-groove-containing electrodes may be expensive and time consuming, it would be desirable if an electrofusion device could be provided that provides variations in electric fields applied to living cells without the use of electrodes having a plurality of concentric grooves.

The device in U.S. Pat. No. 4,441,972 can be used for cell sorting by dielectrophoresis. For cell sorting, the frequency and intensity of an AC voltage that is applied to the electrodes may be varied so that the cells which are desired for collection will arrive at a predetermined radial distance from an opening port and then later be collected and withdrawn through an exit port when the field is relaxed. Rectangular electrical pulses are not used for cell sorting.

The device in U.S. Pat. No. 4,441,972 can also be used for electrofusion. With this manner of use, a low AC voltage is applied to the electrodes in order to allow the cells to contiguously align between the electrodes. Typically a mild AC field of about 10 volts rms at about 250 Khz may be utilized. Then, a single brief unipolar pulse of about 10 to about 250 volts for about 50 microseconds may be applied to cause fusion of the aligned cells. The patent discloses that the frequency, voltage and duration of impulse may be adjusted depending on the type and size of cells to be sorted or fused or upon the type of carrier stream used. In the patent, there is disclosure that various devices, including computers, can be used to control input frequency and voltage to the electrode. However, with particular attention being paid to electrofusion, in U.S. Pat. No. 4,441,972, there is no disclosure of using more than a single pulse for carrying out the electrofusion. It is noted that U.S. Pat. No. 4,476,004 is closely related to U.S. Pat. No. 4,441,972 and has a similar disclosure.

U.S. Pat. No. 4,695,547 discloses a probe for electrofusion, electroporation, and the like. A suitable source of high voltage pulses is disclosed as being capable of providing output voltage pulses in the range of 25–475 Volts at currents up to 1 amp and durations of 1–990 ms. There is no disclosure of using a plurality of Rectangular pulses for carrying out electrofusion or electroporation.

U.S. Pat. No. 4,750,100 discloses a high-voltage and high-amperage switching device capable of delivering an exponential decay pulse or a rectangular wave pulse for electroporation. There is no disclosure of using a plurality of Rectangular pulses for carrying out electroporation or transfection.

U.S. Pat. No. 4,832,814 discloses an electrofusion cell that is used for conducting electrofusion of living cells. An electrical power source provides a series of three pulses, each of 12 microsecond and of 68 volts with a 1 second separation between pulses. It is noted that each pulse has the same voltage and same duration as each other pulse.

U.S. Pat. No. 4,882,281 discloses a probe for electrofusion, electroporation, and the like. Just as disclosed in U.S. Pat. No. 4,695,547 described above, a suitable source of high voltage pulses is disclosed as being capable of providing output voltage pulses in the range of 25–475 Volts at currents up to 1 amp and durations of 1–990 ms. There is no disclosure of using a plurality of pulses for carrying out electrofusion or electroporation.

U.S. Pat. No. 4,910,140 discloses a method for the electroporation of prokaryotic cells by applying high intensity electric fields of short duration. This patent discloses that the pulse will normally consist of a single pulse comprising the entire desired period. Alternatively, the pulse may consist of a plurality of shorter pulses having a cumulative time period coming with desired 2 to 20 msec range. Such a series of pulses must be spaced sufficiently close to one another so that the combined effect results in permeabilization of the cell wall. Typically, such pulses are spaced apart by 5 msec or less, more preferably being spaced apart by 2 msec or less.

U.S. Pat. No. 4,955,378 discloses electrodes for delivering pulses to animal or human anatomical sites for carrying out in vivo electrofusion. It is disclosed that, generally, electrofusion is preferably accomplished under constant voltage conditions by applying to the electrode 3 square waves of 20 volts amplitude and of 20 microsecond duration at a pulse rate of 1 pulse per second. It is noted that each pulse has the same voltage and same duration as each other pulse.

U.S. Pat. No. 5,007,995 discloses a device for electrofusion of living cells. Instead of using unipolar pulses, AC pulses were employed. A series of studies were conducted among the variables of AC frequency, AC voltage applied, and the time duration of the AC pulse. In each study, two of the three variables were held constant, and one variable was varied by setting the variable at different incremental settings. There is no disclosure of using a plurality of Rectangular pulses for carrying out electrofusion.

U.S. Pat. No. 5,019,034 discloses a method for electroporating tissue for the purpose of transporting large molecules into the tissue. Frog skin is used as an example. In carrying out the electroporation, the shape, duration, and frequency of the pulse are selected. The peak voltage is also placed at an initial setting. The pulse is gradually cycled to higher voltages until electroporation occurs. At that point, the pulse shape, duration, frequency, and voltage are maintained until a desired amount of molecular transfer has occurred.

U.S. Pat. No. 5,124,259 discloses a method of electroporation using a specifically defined buffer in which the chloride ion is eliminated. There is a disclosure that, in carrying out the electroporation, the electric field may be 100–1000 V/cm and the time for applying the voltage may be 0.1–50 msec. There is no disclosure of using a plurality of pulses for carrying out the electroporation.

U.S. Pat. No. 5,128,257 discloses several chambers and electrodes used for electroporation. Power supplies provide a voltage range of 200 to 2000 volts. The pulse width is in a range from 0.1 to 100 milliseconds, preferably 1 to 10 milliseconds. There is no disclosure of using a plurality of pulses for carrying out the electroporation.

U.S. Pat. No. 5,134,070 discloses a specially coated electrode on which cells are cultivated. The cells on the electrode are subjected to electroporation. In carrying out the electroporation, a device for measuring electrical field intensity is appropriately interfaced to a micro-processor so that an "intelligent" electroporation device is provided which is capable of applying an ever increasing electrical potential until the cells have porated and which is capable of sensing at what field intensity the cells have porated. Since the device measures the conditions required to induce poration, and detects when poration occurs, substantial reductions in current mediated cell death will be realized since only enough energy to induce poration is introduced into the system. However, it is noted that there is no disclosure of using a plurality of pulses for carrying out electroporation. In addition, the electroporation device is capable of recording information concerning the poration potential required for various cell lines and the effects of various media compositions on the types and sizes of porations that may occur. It is noted, however, that provisions are not made to sustain pore formation that has been induced.

U.S. Pat. No. 5,137,817 discloses an apparatus and method for electroporation using specially designed electrodes for conducting electroporation in vivo. In carrying out the electroporation, a single Unipolar voltage pulse is applied to the host cells. There is no disclosure of using a plurality of pulses for carrying out electroporation.

Each of U.S. Pat. Nos. 5,173,158 and 5,283,194 discloses an apparatus and methods for electroporation and electrofusion in which an electrode is employed that selectively admits cells of a certain size and excludes others. A single pulse generates an electric field which causes electroporation. There is no disclosure of using a plurality of pulses for carrying out either electroporation or electrofusion.

U.S. Pat. No. 5,186,800 discloses, as does U.S. Pat. No. 4,910,140 discussed above, a method for the electroporation of prokaryotic cells by applying high intensity electric fields of short duration. U.S. Pat. No. 5,186,800 also discloses that an applied pulse will normally consist of a single pulse comprising the entire desired period. Alternatively, the pulse may consist of a plurality of shorter pulses having a cumulative time period coming with desired 2 to 20 msec range. Such a series of pulses must be spaced sufficiently close to one another so that the combined effect results in permeabilization of the cell wall. Typically, such pulses are spaced apart by 5 microsec. or less, more preferably being spaced apart by 2 microsec. or less. A series of experiments were conducted to ascertain method parameters which provided maximum cell transformation. In each of the experiments, a single electrical pulse was used to bring about electroporation. Experimental parameters included a number of parameters of the electrical pulse, concentration of the host cells, concentration of the transforming material, and post-shock incubation period. It was observed that the viability and transformability of the cells undergoing electroporation were very sensitive to the initial electric field strength of the pulses. A conclusion reached was that cell survival declines steadily with increasing field strength; and in each of the experiments conducted, the maximum transformation efficiency is reached when 30 to 40% of the cells survive the pulse. There is no disclosure of using a plurality of pulses for carrying out electroporation. In view of the above, it would be desirable if a method of electroporation were provided in which the maximum transformation efficiency were achieved when greater than 40% of cells survive the pulse effecting electroporation.

U.S. Pat. No. 5,211,660 discloses a method for performing an in vivo electrofusion. Details relating to electrical parameters of a unipolar electric field that is utilized are not disclosed.

U.S. Pat. No. 5,232,856 discloses an electroporation device which employs specially designed electrodes. A number of electroporation experiments were conducted using a number of different host cells and different transforming material. In each experiment, only a single Unipolar pulse was applied to the host cells. There is no disclosure of using a plurality of pulses for carrying out electroporation.

U.S. Pat. No. 5,273,525 discloses a syringe based electroporation electrode for drug and gene delivery. In using the electroporation electrode, a conventional power supply is employed which provides from one to one hundred consecutive pulses having a constant pulse amplitude, a constant pulse width, and a constant pulse interval.

Each of U.S. Pat. Nos. 5,304,120 and 5,318,514 discloses an electrode for in vivo electroporation of living cells in a person. In applying electrical energy for bringing about electroporation, a power supply preferably applies electric fields repeatedly, and the amplitude and duration of the electric fields make the walls of the living cells sufficiently permeable to permit drugs or genes to enter the living cells without killing them. The power supply includes a unipolar oscillating pulse train and a bipolar oscillating pulse train. It is noted that, for a chosen pulse train, each pulse rises to the same voltage and has the same duration as each other pulse in a pulse train.

Having discussed a number of theoretical considerations and a number of prior art disclosures, attention is now returned to a further discussion of certain theoretical concepts relating to induction of pore formation in biological cells. It is understood, however, that none of the theoretical concepts discussed herein are intended to limit the scope of the invention. Instead, the scope of the invention is limited only by the claims appended hereto and equivalents thereof.

It has been discovered by the inventors of the present invention that changing pulse parameters during a pulse session reduces damage to cells while maintaining or improving electroporation and electrofusion efficiency. The reduced cell damage can be related to reduced energy applied to the cell. More specifically, two parameters determining total energy applied per pulse are pulse amplitude and pulse width. Variation of pulse width would have different effects than variation of pulse amplitude. Reduction of pulse width following application of a wider pulse would permit application of an above threshold voltage while reducing the total energy in a series of pulses.

Furthermore, for theoretical reasons described below, maintenance of pores already formed in a cell should require less energy than the energy required to initiate a new pore. Variation of pulse width while maintaining an above threshold voltage would be particularly useful in those instances where very small pores are initiated by a wider pulse. Narrower pulses could assist pore expansion in a controlled manner. The ideal condition for any particular type of cell would be to find a set of electrical pulse parameters that would cause pore expansion to a size large enough to permit a foreign molecule (such as a small organic molecule or DNA) to enter the cell without expanding the pore size to one beyond recovery. The pulse parameters to accomplish this goal would have to be experimentally determined for each cell type.

Variation of pulse amplitude would permit application of a below threshold maintanance pulse. Once a pulse of sufficient energy with an above threshold voltage is applied to a cell, a transient decrease in electrical resistance across the cell membrane occurs. Because of the decreased electrical resistance of the cell membrane, pulse voltages below threshold should be sufficient to maintain a cell pore induced by an above threshold pulse.

Thus, while the foregoing body of prior art indicates it to be well known to use electrical pulses to induce electroporation, the prior art described above does not teach or suggest a method of treating materials with pulsed electrical fields which has the following combination of desirable features: (1) provides a process for application of a series of electrical pulses to living cells wherein the electrical pulses produce reduced cell lethality; (2) provides an operator of electrical pulse equipment a process for maximum operator control of an applied pulse series; (3) provides a process for changing pulse width during a series of electrical pulses; (4) provides a process for changing pulse voltage and therefore electric field during a series of electrical pulses; (5) provides a machine for control of the process; (6) provides a pulse protocol that sustains induced pores formed in electroporation; (7) provides a pulse protocol which provides three or more pulses to allow more time for materials to enter cells undergoing electroporation; (8) provides an electrical way to improve cell survival and transfection efficiency; and (9) provides a method of electroporation in which maximum transformation efficiency is achieved when greater than 40% of cells survive the pulse effecting electroporation. The foregoing desired characteristics are provided by the unique method of treating materials with pulsed electrical fields of the present invention as will be made apparent from the following description thereof. Other advantages of the present invention over the prior art also will be rendered evident.

SUMMARY OF THE INVENTION

Electrical pulse sequences are almost infinite in their potential variability. A great variety of pulse sequences are used in the areas of electrical communications and radar. For example, a pulse sequence can be continuous. A continuous pulse sequence can be unipolar or bipolar. A pulse sequence can include rectangular waves or square waves (a special case of rectangular waves). A predetermined number of rectangular pulses, either unipolar or bipolar, can be provided in a gated or burst pulse sequence. In a pulse sequence, pulses can be provided at different levels of amplitude (pulse amplitude modulation); this form of pulse train is used commonly in modems and computer to computer communications. Pulses can be provided with different pulse widths or durations (pulse width modulation); in such a case, a constant pulse interval can be maintained. Pulses can be provided with different pulse intervals (pulse interval modulation); in such a case, a constant pulse width can be maintained.

A specific category of electrical pulse sequences is known as an "agile pulse sequence". For purposes of the present patent, by definition, an agile pulse sequence has the following characteristics: (1) the number of pulses in the sequence can range from 2 to 1,000; (2) the pulses in the sequence are rectangular in shape; (3) each pulse in the sequence has a pulse width; (4) there is a pulse interval between the beginning of a pulse and the beginning of a succeeding pulse in the sequence; (5) pulse amplitude for pulses in the sequence is greater than 100 volts/cm and preferably greater than 200 volts/cm; and (6) pulse polarity can be unipolar or bipolar for pulses in the sequence. Another characteristic in an agile pulse sequence that may be present is that the "on" time of a rectangular pulse in the sequence is less than 10% of the pulse interval.

Although agile pulse sequences have been employed in communications and radar applications, agile pulse sequences have not been employed to treat materials. More specifically, the prior art does not disclose, and the subject invention provides, the use of agile pulse sequences to treat materials to provide very well controlled intense electric fields to alter, manipulate, or serve as a catalyst to cause well defined and controlled, permanent or temporary changes in materials.

More specifically, in accordance with the invention, a method is provided for treating materials, especially organic materials, with pulsed electrical fields, wherein the method includes the step of applying an agile pulse sequence having at least three pulses to a material, wherein the agile pulse sequence has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses.

More specifically, in accordance with the invention, a method is provided for treating materials, especially organic materials, with pulsed electrical fields and includes the step of applying an agile pulse sequence having at least three pulses to a material, wherein at least two of the at least three pulses differ from each other in pulse amplitude.

In accordance with the invention, a method is provided for treating materials, especially organic materials, with pulsed electrical fields and includes the step of applying an agile pulse sequence having at least three pulses to a material, wherein at least two of the at least three pulses differ from each other in pulse width.

In accordance with the invention, a method is provided for treating materials, especially organic materials, with pulsed electrical fields and includes the step of applying an agile pulse sequence having at least three pulses to a material, wherein a first pulse interval for a first set of two of the at least three pulses is different from a second pulse interval for a second set of two of the at least three pulses.

In accordance with another broad aspect of the invention, a method is provided for treating biological cells with pulsed electrical fields to induce pore formation in the cells. The method includes the step of applying an agile pulse sequence having at least three pulses to the cells, wherein the agile pulse sequence has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the cells is maintained.

More specifically, in accordance with the invention, a method is provided for treating biological cells with pulsed electrical fields to induce pore formation in the cells. The method includes the step of applying an agile pulse sequence having at least three pulses to the cells, wherein at least two of the at least three pulses differ from each other in pulse amplitude, such that induced pores are sustained for a relatively long period of time, and such that viability of the cells is maintained.

Further, in accordance with the invention, a method is provided for treating biological cells with pulsed electrical fields to induce pore formation in the cells. The method includes the step of applying an agile pulse sequence having at least three pulses to the cells, wherein at least two of the at least three pulses differ from each other in pulse width, such that induced pores are sustained for a relatively long period of time, and such that viability of the cells is maintained.

Also, in accordance with the invention, a method is provided for treating biological cells with pulsed electrical fields to induce pore formation in the cells. The method includes the step of applying an agile pulse sequence having at least three pulses to the cells, wherein a first pulse interval for a first set of two of the at least three pulses is different from a second pulse interval for a second set of two of the at least three pulses, such that induced pores are sustained for a relatively long period of time, and such that viability of the cells is maintained.

It is clear from the above description that an agile pulse sequence is a class of sequences of non-sinusoidal electrical pulses. In this respect, in accordance with the principles of the invention, other categories of non-sinusoidal electrical pulse sequences can be employed for treating materials aside from agile pulse sequences.

In this respect, in accordance with a broader aspect of the invention, a method is provided for treating material with pulsed electrical fields and includes the step of applying a sequence of at least three non-sinusoidal electrical pulses, having field strengths equal to or greater than 100 V/cm and preferably equal to or greater than 200 V/cm, to the material. The sequence of at least three non-sinusoidal electrical pulses has one, two, or three of the following characteristics: (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses. Preferably, the material is an organic material.

In accordance with another broad aspect of the invention, a method is provided for treating biological cells with pulsed electrical fields to induce pore formation in the cells and includes the step of applying a sequence of at least three non-sinusoidal electrical pulses, having field strengths equal to or greater than 100 V/cm and preferably equal to or greater than 200 V/cm, to biological cells. The sequence of at least three non-sinusoidal electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses, such that induced pores are sustained for a relatively long period of time, and such that viability of the cells is maintained. The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In view of the above, it is an object of the present invention is to provide a method of treating materials with pulsed electrical fields which provides a process for application of a series of electrical pulses to living cells wherein the electrical pulses produce reduced cell lethality.

Still another object of the present invention is to provide a method of treating materials with pulsed electrical fields that provides an operator of electrical pulse equipment a process for maximum operator control of an applied pulse series.

Yet another object of the present invention is to provide a method of treating materials with pulsed electrical fields which provides a process for changing pulse width during a series of electrical pulses.

Even another object of the present invention is to provide a method of treating materials with pulsed electrical fields that provides a process for changing pulse voltage during a series of electrical pulses.

Still a further object of the present invention is to provide a method of treating materials with pulsed electrical fields which provides a machine for control of the process.

Yet another object of the present invention is to provide a method of treating materials with pulsed electrical fields that provides a pulse protocol that sustains induced pores formed in electroporation.

Still another object of the present invention is to provide a method of treating materials with pulsed electrical fields which provides a pulse protocol which provides three or more pulses to allow more time for materials to enter cells undergoing electroporation.

Yet another object of the present invention is to provide a method of treating materials with pulsed electrical fields that provides an electrical way to improve cell survival and transfection efficiency.

Still a further object of the present invention is to provide a method of treating materials with pulsed electrical fields that provides a method of electroporation in which maximum transformation efficiency is achieved when greater than 40% of cells survive the pulse effecting electroporation.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIGS. 3A, 3B, and 3C together form an electrical schematic circuit diagram of the high voltage assembly. More specifically, FIG. 3A presents circuitry for a pulse amplitude control. FIG. 3B presents circuitry for a reservoir capacitor. FIG. 3C presents circuitry for a pulse switch.

FIGS. 5A, 5B, 5C, and 5D together form an electrical schematic diagram of an I-O (input-output) assembly. More specifically, FIG. 5A presents a schematic diagram for I-O control circuitry. FIG. 5B presents a schematic diagram for digital-to-analog converter (DAC) circuitry. FIG. 5C presents a schematic diagram for circuitry for connecting with a pulse generator and connecting with a low voltage power supply. FIG. 5D presents a schematic diagram for load fault detection circuitry.

FIG. 11 is a bottom view of the upper body section shown in FIG. 6.

FIG. 12 is a cross-sectional view of the upper body section shown in FIG. 11 taken along line 12—12 thereof.

FIG. 13 is a side view of the upper body section shown in FIG. 11.

FIG. 14 is top view of the middle body section shown in FIG. 6.

FIG. 15 is a cross-sectional view of the middle body section shown in FIG. 14 taken along line 15—15 thereof.

FIG. 16 is a side view of the middle body section shown in FIG. 14.

DETAILED DESCRIPTION

Figure 1:
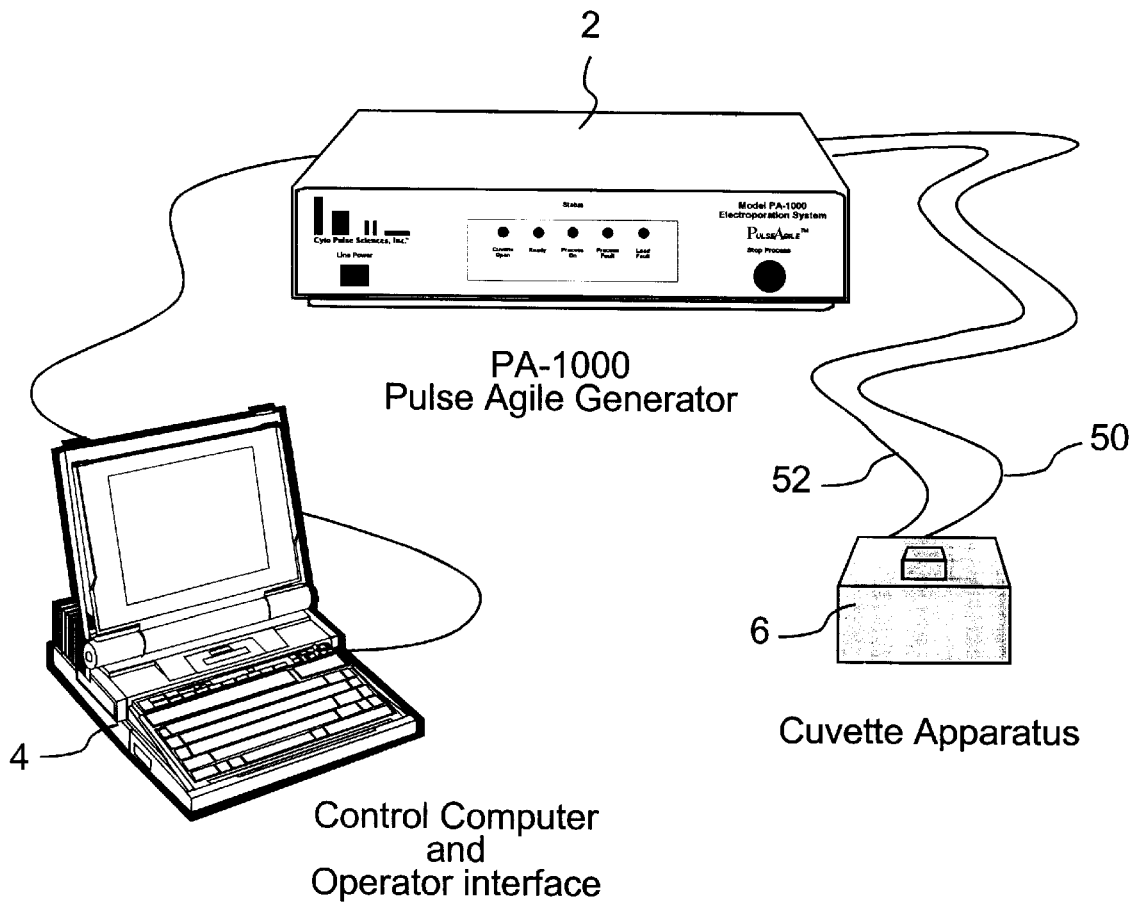
FIG. 1 is a perspective view of the overall apparatus used to carry out the method of the invention of treating materials with pulsed electrical fields.

This invention involves a process for applying electrical pulses to living cells for the purpose of electroporation or electrofusion. The parameters of pulse width and pulse voltage can be changed from pulse to pulse by prior hardware or software programming. An important object of applying pulses of changing voltage and width is to maximize the desired result of electroporation or electrofusion and minimize lethal damage to cells. This object may be achieved by optimizing the energy applied to cells through reduction of applied energy after an initial higher energy pulse.

Conventional theory in the fields of electroporation and electrofusion teaches that a threshold voltage must be exceeded to achieve cell electroporation or electrofusion. In implementing the conventional theory, a single pulse is employed by applying a pulse with a voltage above threshold. Moreover, the single pulse concept is extended in conventional theory to include a series of pulses without accounting for the changes in cell membrane resistance induced by the first above-threshold pulse. The inventors of the subject invention described herein have realized that changes in cell membrane resistance induced by the first above-threshold pulse should be taken into consideration in applying subsequent pulses. It also is accepted in conventional theory that the energy of a pulse is as important as the voltage of a pulse. Within limited parameters, decreasing pulse width has the same effect as decreasing pulse voltage. Again, conventional wisdom does not take into consideration the altered electrical resistance following the first pulse when sequential pulses of equal energy are applied.

The diameter of a pore induced in a cell is increased by increasing energy. Beyond a critical energy level that is dependent upon cell type and size, a pore is created that destroys the cell by unlimited expansion. Cell structures such as the cell cytoskeleton, limit the expansion of cell pores. Maximum poration is achieved by a maximum number of pores of a size as close to but not larger than the pore size that results in unlimited pore expansion.

It is understood that the metes and bounds of the subject invention are not bound by theoretical considerations. However, for purposes of better understanding of the use and operation of the subject invention, a brief theoretical explanation may be helpful. More specifically, in accordance with new theoretical considersations set forth by the inventors herein, if an applied pulse initiates pore formation in a cell and that pulse is followed by a pulse of lesser energy, the second pulse would have the effect of expanding the pore at a slower rate than a pulse of full initial energy. Pulses of continually decreasing energy would have the effect of even slower pore expansion thus allowing a greater control of pore expansion nearer the critical maximum pore size.

As stated above, conventional theory relating to electroporation does not discuss an occurrence of decreased cell membrane resistance with continually expanding pore size. However, it is appreciated by the inventors herein that this decreased resistance may actually result in less effect of the applied voltage because the local voltage decreases in proportion with the decreased local resistance. This would result in additional attenuation of the tendency to expand pore size. In this respect, conventionally applied pulse trains may expand pores too rapidly to take advantage of this natural attenuation of pore expansion. It is the inventors' appreciation that approaching maximum pore size through the application of stepwise decreasing or continually decreasing the pulse energy in a train of pulses would permit maximum usage of the natural attenuation of pore size expansion through decreased cell membrane resistance.

Electroporation of a cell is a heterogenous process for several reasons. First, cells are roughly round and the electrical force upon the cell membrane is proportional to the angle of the cell membrane relative to the direction of current. The greatest force is at the site of the cell where the cell membrane is perpendicular to the current. Second, cell membranes are ireregular in shape. Some cells have projections that have cell membrane sections perpendicular to the current at sites distant to the site nearest to the electrode. Irregularities is cytoskeleton contribute to heterogenous electroporation.

Irregular electroporation makes maximization of electroporation difficult because if only one pore expands beyond rupture, the cell will die. This makes it imperative to develop a technique that gently expands pores after pore initiation. The subject invention satisfies this need.

With reference to the drawings, apparatus for carrying out the method of treating materials with pulsed electrical fields embodying the principles and concepts of the present invention are illustrated.

The apparatus employed for carrying out the method of treating material with pulsed electrical fields of the invention includes the Model PA-1000 Electroporation System of Cyto Pulse Sciences, Inc., Columbia, Md., shown in FIG. 1. The Model PA-1000 Electroporation System is designed to accomplish a wide range of electroporation tasks, many of which are not possible with existing equipment. Some of the new tasks that can be carried out by the Model PA-1000 Electroporation System include: changing pulse width from one pulse to the next; changing pulse amplitude from one pulse to the next; changing pulse interval from one pulse to the next; producing a high fidelity pulsed electric field, effectively independent of load; providing a pulse amplitude monitor which gives a very accurate replica of high voltage pulses; providing a pulse current monitor which gives a very accurate replica of pulse current; providing a computer-generated agile pulse sequence; and providing automatic data logging and recall of each pulse sequence used. As a result, the Model PA-1000 Electroporation System provides a sequence of very finely controlled, high fidelity, pulsed electric fields to electroporate a wide variety of substances including plant and mammalian cells.

The Model PA-1000 Electroporation System includes three major components: a high voltage agile pulse sequence generator 2 (known as Pulse Agile (TM) generator); a combined control computer and computer interface 4; and a cuvette apparatus 6. The cuvette apparatus 6 operates with standard 0.4 cm, 0.2 cm and 0.1 cm cuvettes. Custom interfaces are available for other cuvette holders and delivery systems. The Model PA-1000 Electroporation System specifications are contained in the Specifications Table presented below.

Specifications Table
for Model PA-1000 Electroporation System

PULSE PARAMETERS

| Voltage: | | Field Strength vs Cuvette Used | |
| --- | --- | --- | --- |
| | 0.4 cm | 0.2 cm | 0.1 cm |
| Minimum 25 volts | 40 v/cm | 80 v/cm | 160 v/cm |
| Maximum 1000 volts | 2500 v/cm | 5000 v/cm | 10,000 v/cm |

Time Required to Change Amplitude (previous pulse to next pulse)

| | |
| --- | --- |
| Increase | 160 ms/100 volts |
| Decrease | 62 × ln[previous/next] milliseconds |
| Maximum Pulse Current | 100 amps |
| Pulse Drop | <0.07%/$\mu$s into 10 ohms |

Width:

| | |
| --- | --- |
| Rise Time | <100 ns |
| Width | <1 $\mu$s to 8,000 $\mu$s |
| Width Step Size | 0.125 $\mu$s |

Interval:

| | |
| --- | --- |
| Minimum | 0.1 seconds (a function of amplitude change) |
| Maximum | 4,000 seconds |
| Interval Step Size | 1 $\mu$s |

MODES

Continuous
Agile Pulse Sequence

-continued

Specifications Table
for Model PA-1000 Electroporation System

Figure 2:
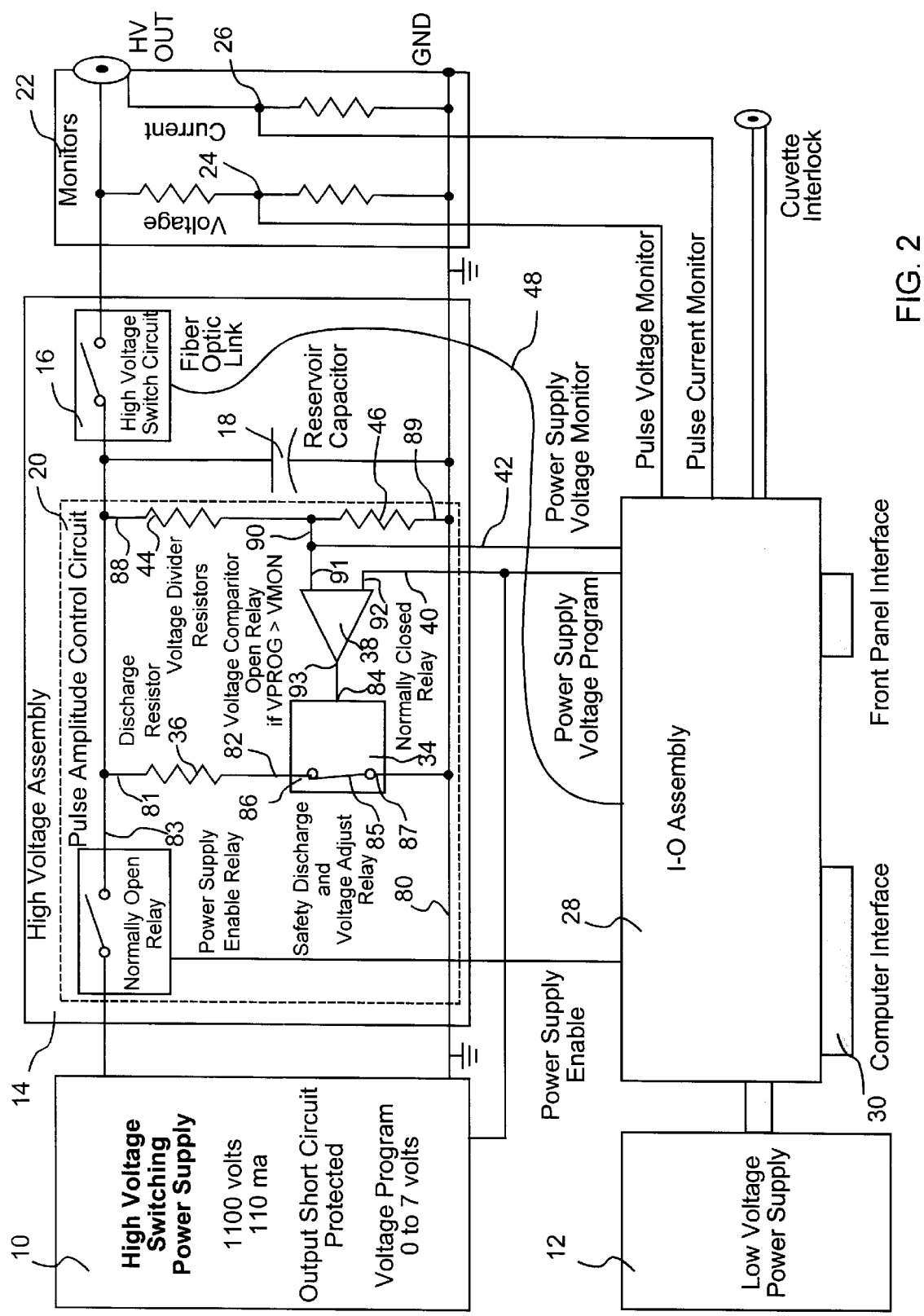
FIG. 2 is a block diagram, partially in schematic form, showing major functional assemblies of the overall apparatus shown in FIG. 1.
Figure 3C:
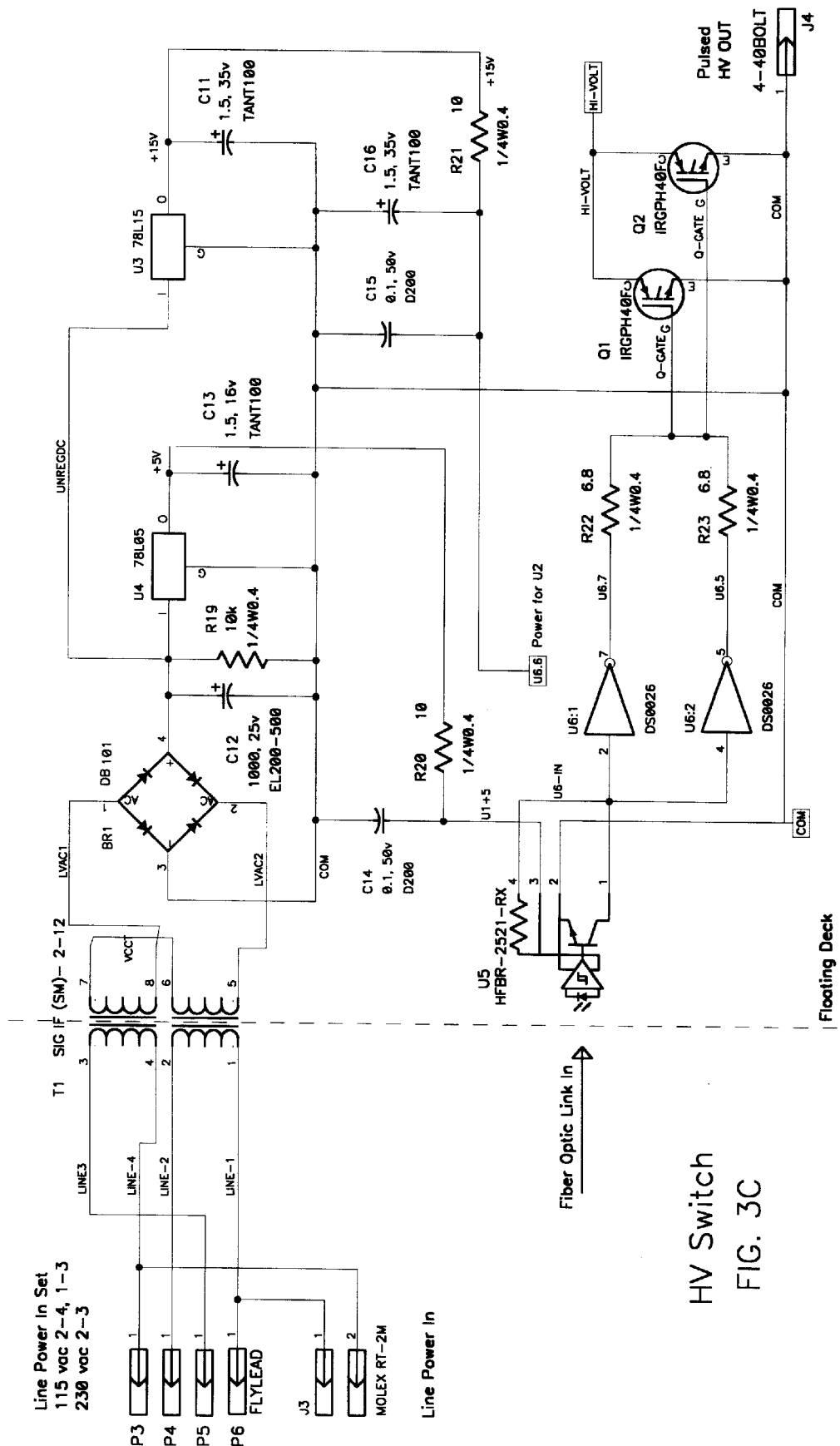

20 Groups; Pulse Parameters Constant Within Group; from 1 to 100 pulses
Continuous Mode Selectable at End of Any Group
FRONT PANEL STATUS LED'S Cuvette Holder Open
Pulser Ready
Process On
Process Fault
Load Fault
WINDOWS OPERATOR INTERFACE Set-up of Pulse Sequence
Automatic Save of Sequence File with Unique File Name
SAFETY Pulser will not operate when cuvette holder open
Front Panel Sequence Stop Button
Pulse Shut Down on Detection of Load Fault More specifically with respect to the agile pulse sequencer 2 (known as Pulse Agile (TM) generator), the basic pulser topology includes a grounded reservoir capacitor 18 and a single floating high voltage switch assembly 16 (see FIGS. 2 and 3C). When the switch assembly 16 is closed, it connects the reservoir capacitor 18 to the load, which is the cuvette assembly 6. This permits current to flow to the load. In this topology the reservoir capacitor 18 must be sufficiently large to supply load current for the duration of the pulse. In this design the reservoir capacitor 18 is sized at 156 uf. This is sufficient to drive a 10 ohm load for 100 us with the voltage on the capacitor dropping less than 7%. A 1000 volt 100 ma power supply is used to rapidly charge the large reservoir capacitor to the voltage required for the next pulse. If the next pulse has a larger or smaller amplitude than the preceding pulse, the voltage on the large capacitor 18 must be rapidly changed before the arrival of the next pulse. This is accomplished by specially designed circuits in the Pulse Amplitude Control Circuit 20. The pulse voltage monitor circuitry 24 and the current voltage monitor assembly 26 provide replicas of the pulse voltage and pulse current, respectively. These values are used to calculate the resistance of the material being porated. The high voltage switch circuit in this topology must float since one end is always connected to the high voltage. The pulse signal is delivered to the switch assembly 16 via a fiber optic cable 48 which is not electrically conductive.

The agile pulse sequence generator 2 produces the agile pulse sequence from instructions sent from the combined control computer and interface 4. The pulser also contains safety circuits to immediately shut down the pulse in the case of a process fault or load fault. A process fault occurs if the cuvette apparatus is opened during the pulse sequence or if the process stop button is depressed during a pulsing sequence. A load fault occurs if the high voltage output is connected to a short circuit.

There are five major assemblies in the pulser: (a) High Voltage DC Power Supply assembly 10; (b) Low Voltage DC Power Supply assembly 12; (c) High Voltage Assembly 14 (which includes Pulse Switch Circuit 16, Reservoir Capacitor 18, and Pulse Amplitude Control Circuit 20); (d) Monitor Assembly 22 (which includes Pulse Amplitude Monitor Circuitry 24 and Current Monitor Circuitry 26); and (e) I-O (input-output) Assembly 28 which is connected to the computer interface 30 portion of the combined computer and interface 4. The computer interface 30 which is connected to the computer portion 32 of the combined computer and interface 4. Each assembly is described below in greater detail. The High Voltage DC Power Supply 10 assembly is a modified commercial 1000 volt, 100 milliamp supply. The output voltage is controlled by a program voltage signal generated by the computer 32 and Digital to Analog Converter (DAC) in the I-O assembly 28. The 0 to 7 volts input signal will produce a 25 to 1000 volt output. The power supply 10 has a maximum charge rate of 100 milliamps and can completely charge the 156 uf reservoir capacitor 18 from 0 to 1000 volts in 1.6 seconds. The power supply 10 has short circuit protection and can operate indefinitely into a shorted output. The regulation is better than 0.1% from 20 to 100 milliamps.

The Low Voltage DC Power Supply assembly 12 is a commercial +12 volt, +5 volt, 35 watt power supply used in many industrial applications. This supply is used to power the I-O assembly 28 and the Pulse Amplitude Control Circuit.

The Pulse Amplitude Control (PAC) Circuit 20 of the High Voltage Assembly 14 is a unique circuit used to rapidly decrease the reservoir capacitor 18 to the desired amplitude of the next pulse. In terms of its structural arrangement, the Pulse Amplitude Control (PAC) Circuit 20 is an electrical control circuit for connection between a high voltage power supply 10 and a high voltage switch assembly 16 and connection across a capacitor 18 and a ground 80, for controlling discharge from the capacitor 18 through the high voltage switch assembly 16. This electrical control circuit includes a discharge resistor 36 which has a first resistor connection 81 and a second resistor connection 82. The first resistor connection 81 is connected to a high voltage terminal 83. A relay 34 includes a relay input 84 and a normally closed switch 85 and has a first switch connection 86 and a second switch connection 87. The second resistor connection 82 of the discharge resistor 36 is connected to the first switch connection 86, and the second switch connection 87 is connected to the ground 80. A voltage divider assembly has a first divider connection 88 connected to the high voltage terminal 83. A second divider connection 89 is connected to the ground 80, and a third divider connection 90 is located between the first and second divider connections. A voltage comparator assembly 38 includes a first comparator input connection 91, a second comparator input connection 92, and a comparator output connection 93. The comparator output connection 93 is connected to the relay input 84. The first comparator input connection 91 is connected to the third divider connection 90. The first comparator input connection 91 is further connected to a power supply voltage monitoring output 42, and the second comparator input 92 is connected to a power supply voltage programmed output 40.

In terms of the performance of the above-described Pulse Amplitude Control Circuit 20, a very large capacitor is needed to store enough energy to prevent the pulse from drooping during long pulses into low impedance loads. This pulsing application requires this large capacitor because of the low impedances of the biologic material being electroporated. On the other hand, a very small capacitor is needed if the voltage of the pulse is to be changed rapidly. These are conflicting requirements. The inventive solution to the problem created by these conflicting requirements is to size the reservoir capacitor 18 to hold the pulse droop to less than 7% at 100 ms into 10 ohms. To change the pulse amplitude a discharge circuit rapidly discharges the capacitor 18 to make possible pulse intervals as short as 0.1 second. This is accomplished by using a high voltage relay 34 to place a 300 ohm discharge resistor 36 across the capacitor 18. This provides an RC time constant of 52 milliseconds which is less than the 100 ms minimum pulse interval. The voltage comparator 38 is used to determine if the relay 34 should be closed. Two voltages are used, the power supply program voltage by way of line 40 connected to the I-O (input-output) Assembly 28 plus a 0.2 volt bias for hysterisis and the power supply monitor voltage by way of line 42 connected to the I-O (input-output) Assembly 28. The power supply monitor circuitry includes a resistive voltage divider connected across the reservoir capacitor 18. The resistive voltage divider includes first resistor 44 having the first divider connection 88 and sharing the third divider connection 90 with the second resistor 46 which also includes the second divider connection 89. The resistive voltage divider produces an output voltage which is usually identical to the program voltage. If the voltage on the next pulse is less than the previous pulse, the program voltage is decreased to the desired level. This creates a difference between the program voltage and the voltage monitor circuitry which is reading the voltage of the reservoir capacitor 18 (without the discharge circuit this level would take several minutes to decay). When this differential condition occurs, the voltage comparator circuit 38 closes the discharge relay 34. When the reservoir capacitor voltage bleeds down and the voltage monitor reaches the level of the program voltage, the comparator 38 is in equilibrium, and the discharge relay 34 is opened. This same circuit also operates as the safety dump to insure the capacitor 18 is discharged when the unit is not operating. The relay 34 is normaly closed, so when power is removed, the relay closes. An electrical schematic diagram of the Pulse Amplitude Control Circuit 20 is presented in FIG. 3A.

Figure 5A:
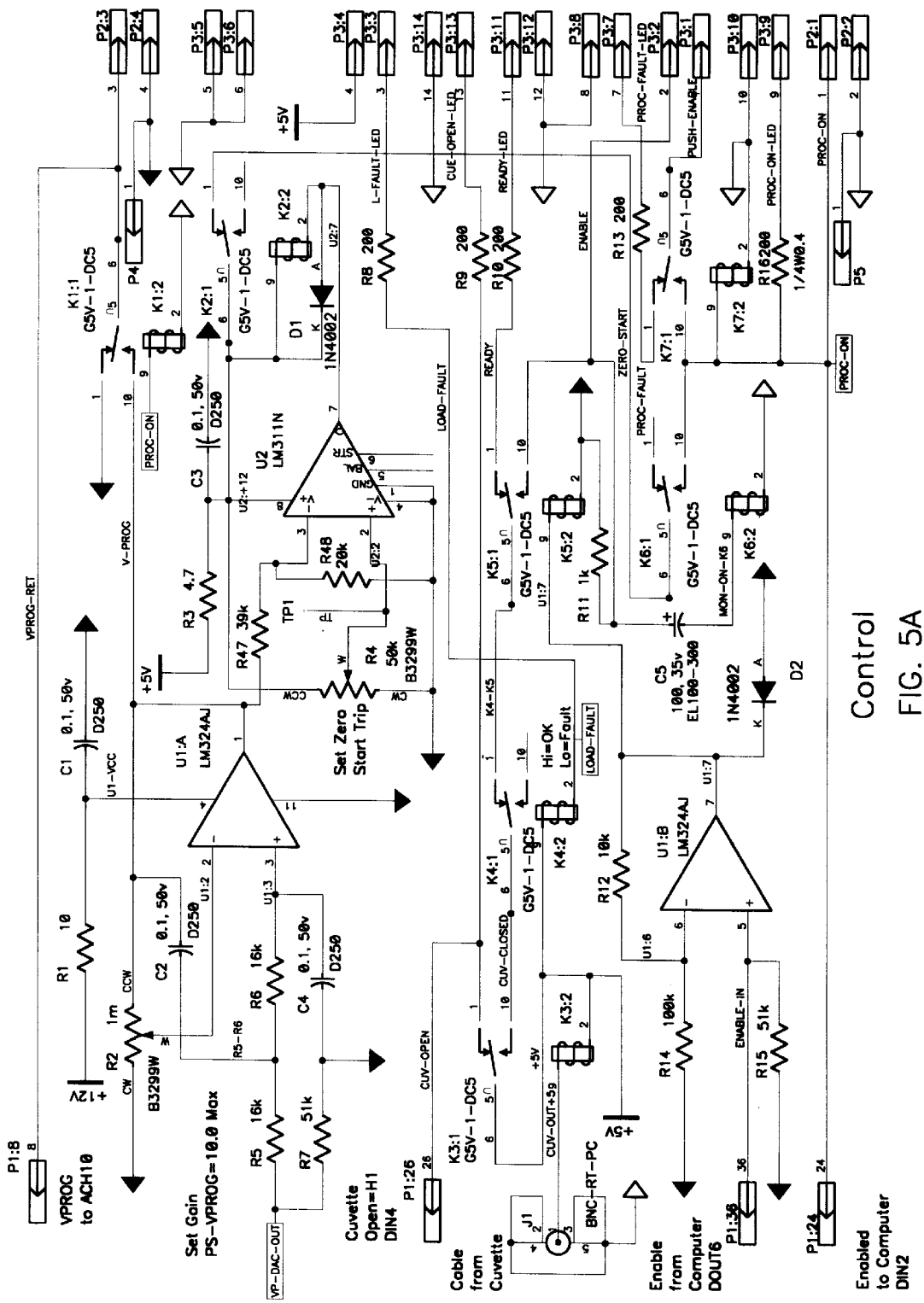
Figure 5B:
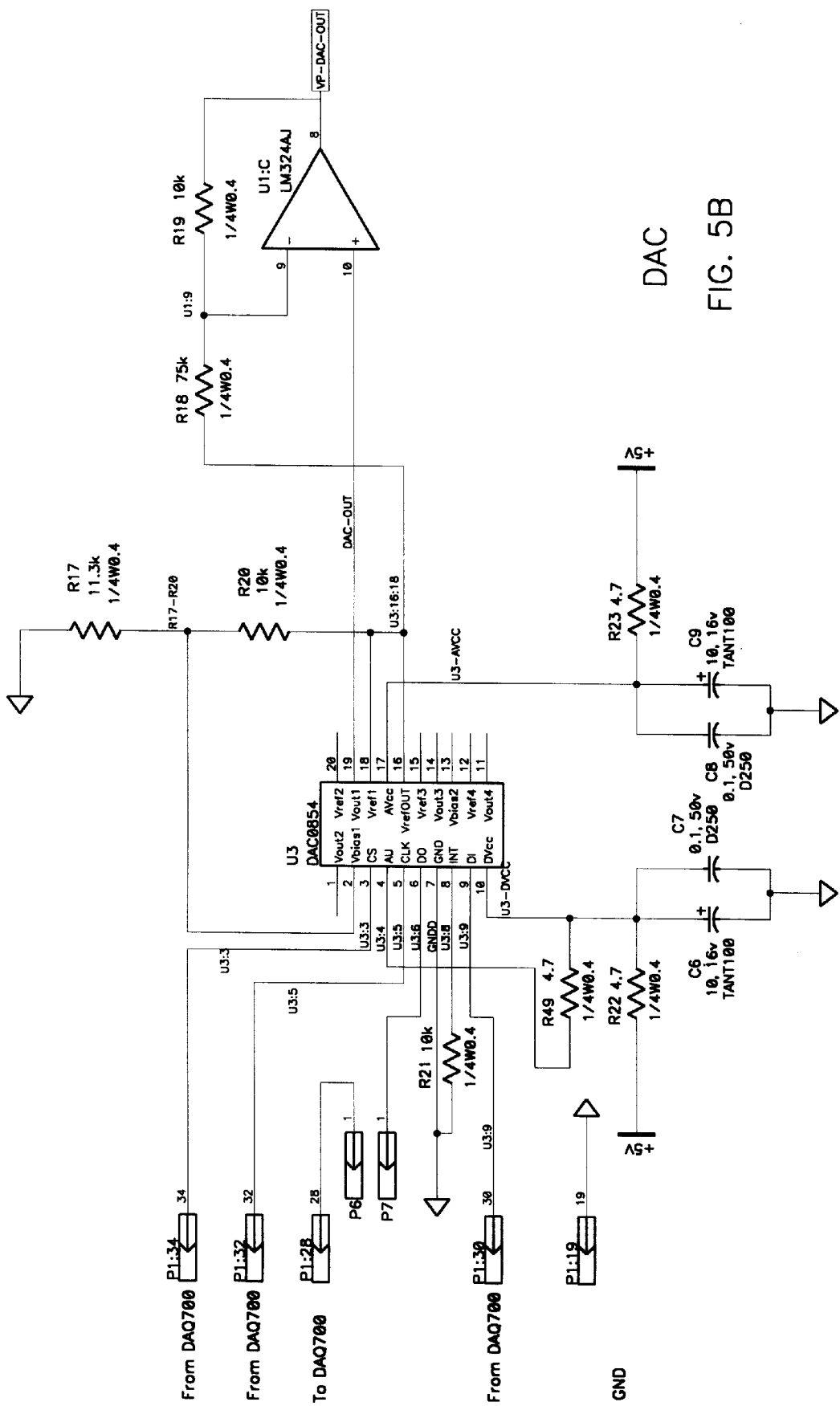

The Reservoir Capacitor 18 of the High Voltage Assembly 14 is a custom design which permits the rapid charging and discharging required in a small volume. It consist of three electrolytic capacitors in series with three polyester capacitors. The polyester capacitors provide the rapid initial charge required, and the electrolytics, which respond slower, provide the charge for the longer pulses. The schematic is presented in FIG. 5B.

Figure 5C:
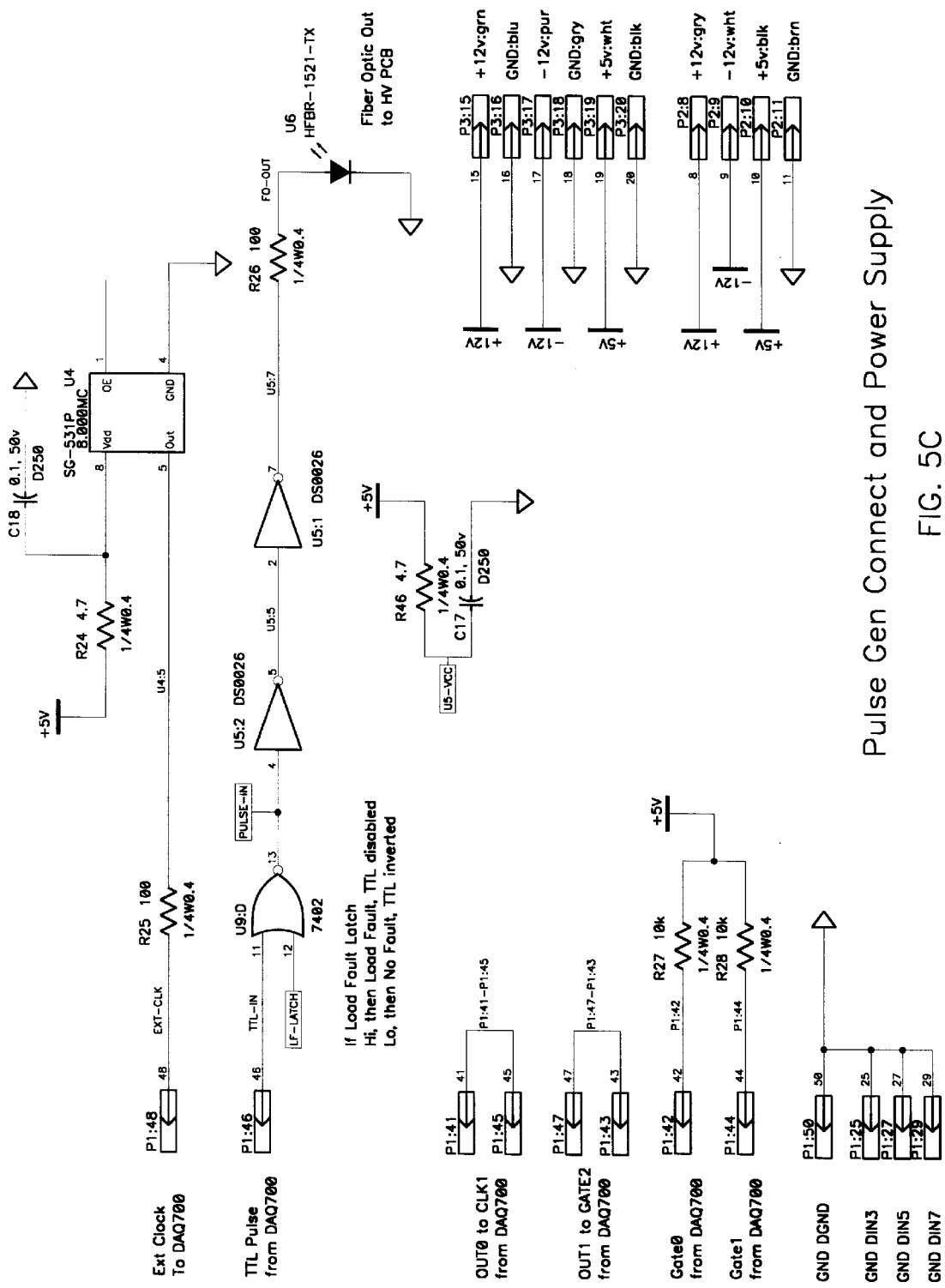

The Pulse Switch of the High Voltage Assembly has demanding requirements. It must open in 100's of nanoseconds while switching up to 100 amps of current at 1000 volts, a peak power of 100,000 watts. An Insulated Gate Bipolar Transistor (IGBT) is employed to meet these requirements. Since the switch floats at the power supply voltage, external connections to the switch must be isolated. The line power is supplied via an isolation transformer. The pulse drive signal is supplied via a fiber optic cable. Light on indicates pulse on. A fiber optic receiver is used to convert light back to electricity. This pulse is then amplified and used to drive the IGBT. A schematic is presented in FIG. 5C.

Figure 4:
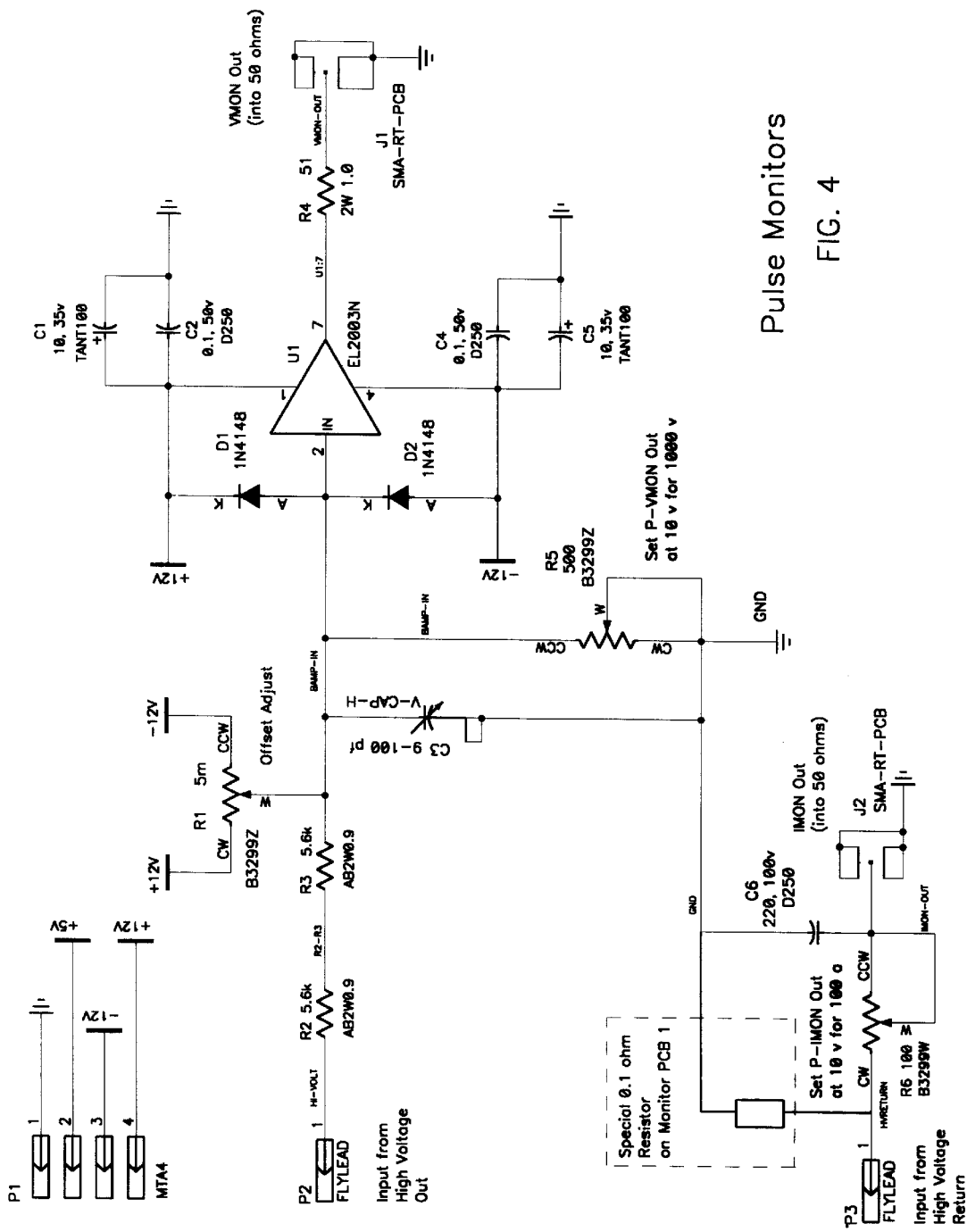
FIG. 4 presents circuitry for a monitor assembly.

The Monitor Assembly of the High Voltage Assembly includes two monitors, the pulse amplitude monitor and the pulse current monitor. A pulse voltage monitoring circuit includes a voltage divider at the pulser output. The divided voltage is then compensated and buffered. A 0 to 1000 volt pulse produces a 0 to 10 volts output. The output is used to drive an oscilloscope or an analog to digital converter. A pulse current monitoring circuit includes a very small current viewing resistor in the return leg of the output. The voltage developed across this resistor is a linear function of the current through the resistor by Ohms law. A 0 to 100 amp pulse current provides a 0 to 0 10 volt monitor output. The output of the two monitors may be used to accurately calculate the load resistance. A schematic is presented in FIG. 4.

The I-O Assembly interfaces to the computer and has six functions: (1) converts computer digital word into an analog power supply program voltage; (2) generates the clock signal for the pulse generator in the computer; (3) interfaces computer to control and safety circuits; (4) interfaces computer to load fault circuit; (5) converts computer generated pulses into light for fiber optic transmission; and (6) provides a general interface connection to the computer. An annotated schematic diagram is presented for the I-O Assembly in FIGS. 5A, 5B, 5C, and 5D.

The Control Computer is connected to the I-O Assembly and performs the following functions: (1) operator set up, in Window format, of pulse sequence; (2) file management; (3) generates the control for the pulse width, pulse interval, pulse amplitude, and number of pulses; and (4) performs safety function controls.

The computer hardware is a personal computer (PC) compatible with a data acquisition board or a microprocessor. The software is written in assembly, C and Visual C++ and operates under Windows.

The computer software performs the following:
1. Checks for Pulser Line power on.
2. Checks for cuvette interlock being closed; if cuvette holder is open, the system does not continue.
3. Prompts operator to enter agile pulse sequence which includes:
   (a) number of pulses;
   (b) pulse voltage;
   (c) pulse width; and
   (d) pulse interval.
4. Checks pulse input parameters in each of the following groups:
   (a) N>1 and <50, or continuous;
   (b) pulse width 1 to 4000 microseconds;
   (c) pulse interval 0.1 to 5,000 seconds;
   (d) pulse amplitude 25 to 1000 volts;
   (e) interval for amplitude decrease to next pulse>62*In (PAprevious/PAnext); and
   (f) interval for amplitude increase to next pulse>5.6 ms/volt.
5. Enables (turns on power supply).
6. Reads Power Supply Voltage Monitor.
7. Waits two seconds.
8. Starts pulse sequence and sends pulse parameter commands as required.
9. Monitors process fault signal from I-O Assembly.
10. Monitors load fault signal from I-O Assembly.
11. When complete, disables.
12. Stores pulse sequence values in file.

The cuvette apparatus 6 is connected to the high voltage assembly 20 in the agile pulse generator 2 by two coaxial cables. One is the high voltage pulse cable 50; the second is the interlock cable 52. The interlock cable 52 completes a circuit which satisfies the interlock circuit. The interlock circuit includes a magnetic element 54 in the cover 56 of the cuvette apparatus 6. The interlock magnetic element 54 is bonded in a V-groove on an interior side of the cover 56. The cover 56 must be closed for the interlock to be satisfied. The cuvette apparatus 6 uses standard 0.1, 0.2 and 0.4 cm cuvette. Detailed drawings of the cuvette apparatus 6 are presented in FIGS. 6–18.

Figure 6:
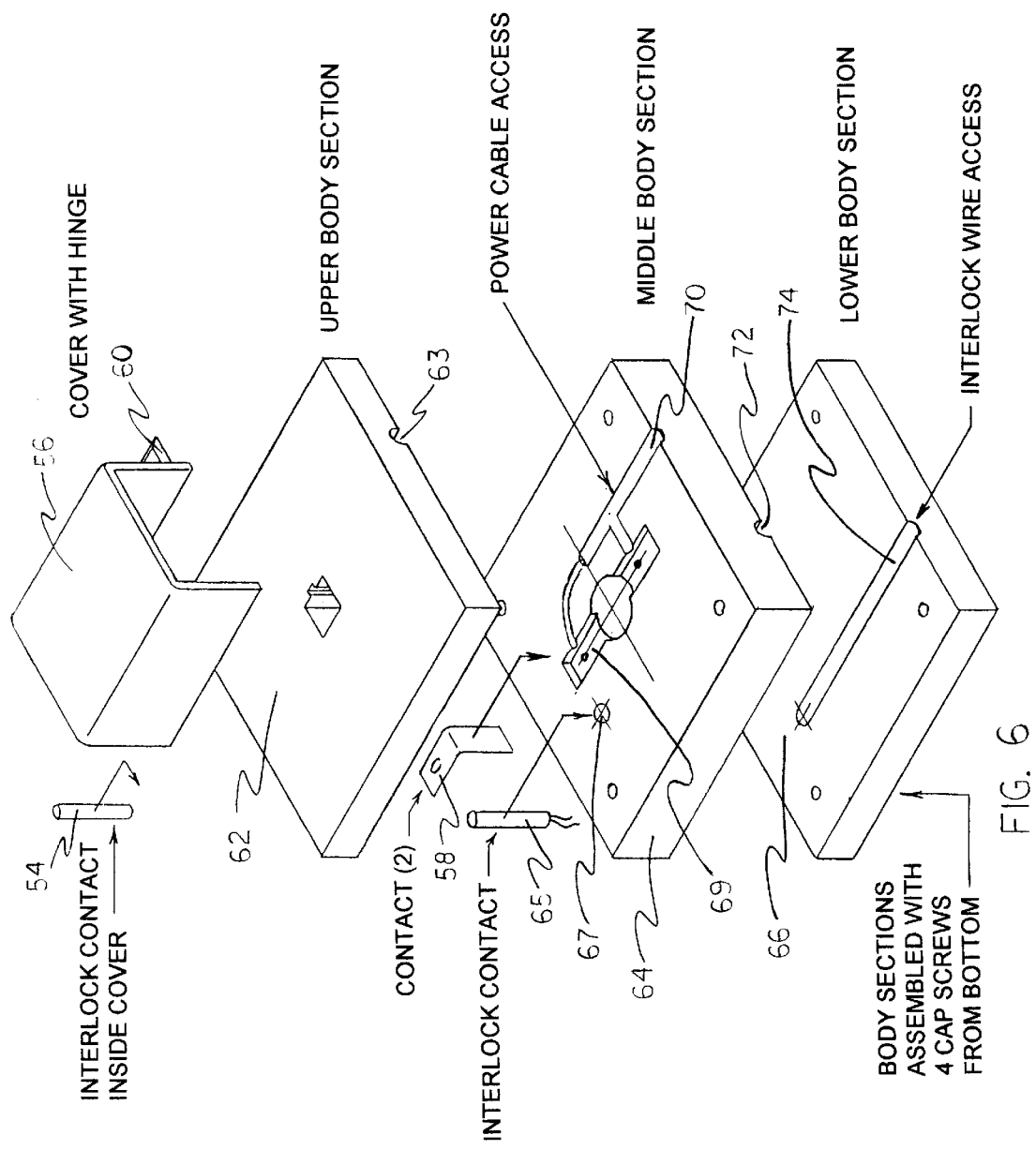
FIG. 6 shows an exploded perspective view of the overall cuvette apparatus.

FIG. 6 shows an exploded perspective view of the overall cuvette apparatus 6.

Figure 7:
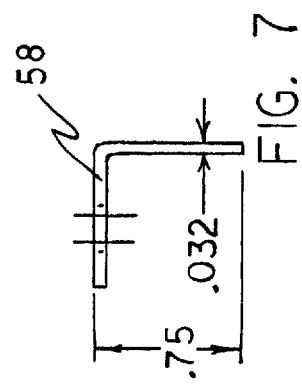
FIG. 7 is side view of a contact shown in FIG. 6.

FIG. 7 is side view of a contact 58 shown in FIG. 6. There are two contacts 58 employed. The contacts 58 are mounted by screws onto the middle body section 64.

Figure 8:
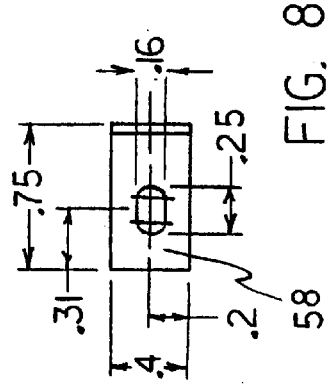
FIG. 8 is a bottom view of the contact shown in FIG. 7.

FIG. 8 is a top view of the contact 58 shown in FIG. 7.

Figure 9:
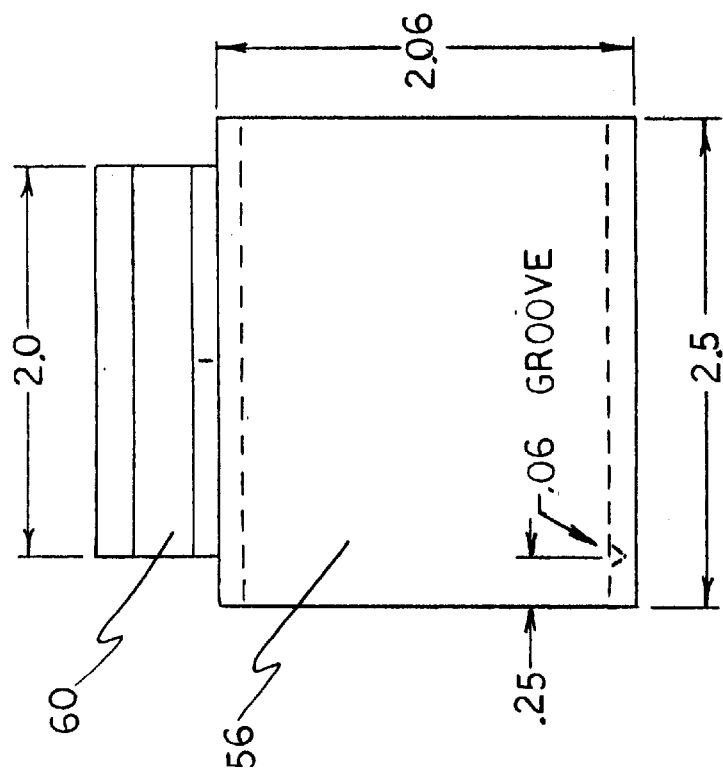
FIG. 9 is top view of the cover shown in FIG. 6.

FIG. 9 is a top view of the cover 56 shown in FIG. 6. The cover 56 includes an acrylic hinge 60.

Figure 10:
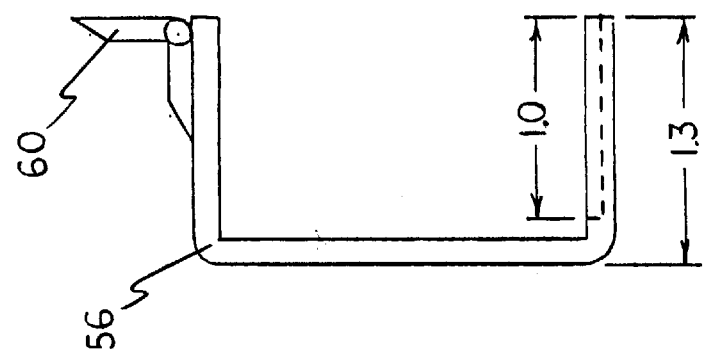
FIG. 10 is a side view of the cover shown in FIG. 9.

FIG. 10 is a side view of the cover 56 shown in FIG. 9.

FIG. 11 is a bottom view of the upper body section 62 shown in FIG. 6. The upper body section 62 includes grooves 63 for receiving power cables that are connected to the contacts 58.

FIG. 12 is a cross-sectional view of the upper body section 62 shown in FIG. 11 taken along line 12—12 thereof.

FIG. 13 is a side view of the upper body section 62 shown in FIG. 11.

FIG. 14 is a top view of the middle body section 64 shown in FIG. 6. The middle body section 64 receives the contacts 58. An interlock contact 65 is received by the middle body section 64 in a reception channel 67. The middle body section 64 also includes contact-receiving wells 69 for receiving portions of the contacts 58. The middle body section 64 includes grooves 70 for receiving power cables connected to the contacts 58. The grooves 63 in the upper body section 62 and the grooves 70 in the middle body section 64 are placed in registration when the upper body section 62 is connected to the middle body section 64, and the power cables are contained in access channels provided by the grooves 63 and the grooves 70. The middle body section 64 also includes a groove 72 for providing access for an interlock contact wire.

FIG. 15 is a cross-sectional view of the middle body section 64 shown in FIG. 14 taken along line 15—15 thereof.

FIG. 16 is a side view of the middle body section 64 shown in FIG. 14.

Figure 17:
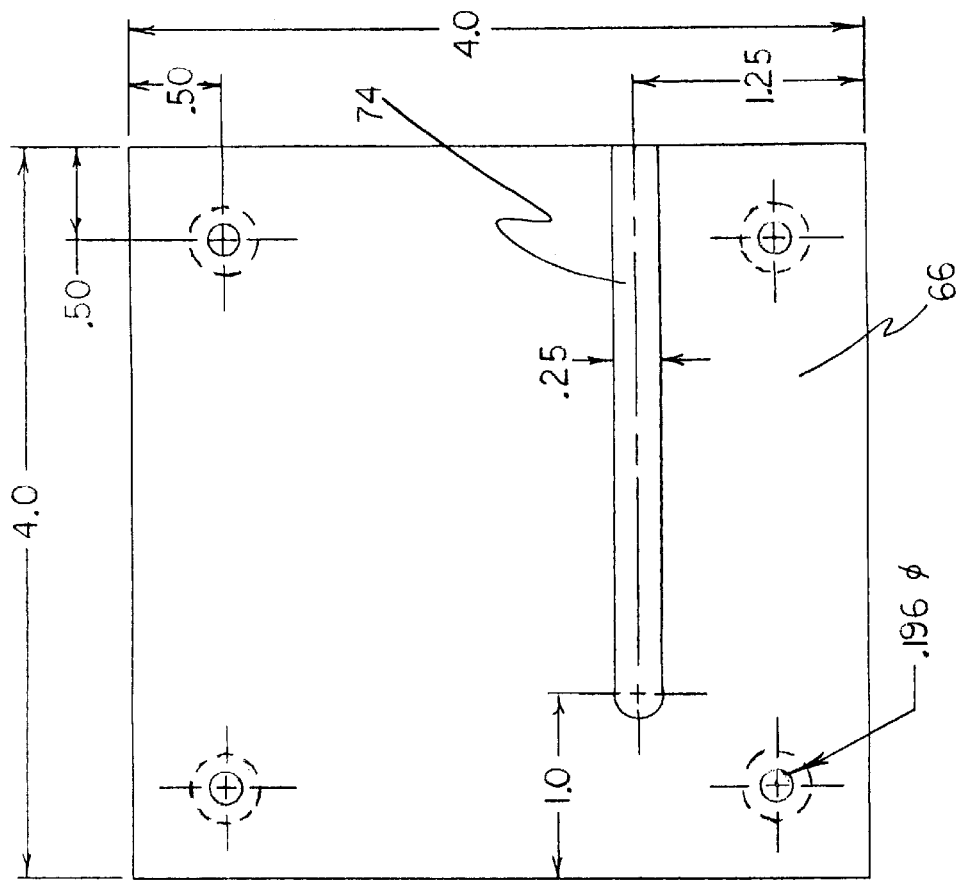
FIG. 17 is top view of the lower body section shown in FIG. 6.

FIG. 17 is a top view of the lower body section 66 shown in FIG. 6. The lower body section 66 includes a groove 74 which provides access for an interlock wire. When the middle body section 64 and the lower body section 66 are connected together, the groove 72 in the middle body section 64 and the groove 74 in the lower body section 66 are placed in registration, and the interlock wire is contained in an access channel provided by the groove 72 and the groove 74.

Figure 18:
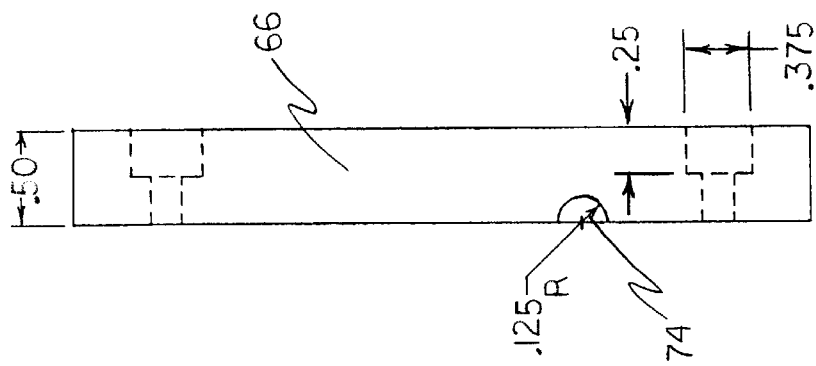
FIG. 18 is a side view of the lower body section shown in FIG. 17.

FIG. 18 is a side view of the lower body section 66 shown in FIG. 17.

Turning to results obtained by employing the above-described apparatus for carrying out the method of the invention, Table I set forth herein is a tabulation of results of experiments which compare employing principles of the invention and employing conventional principles for carrying out electroporation. In carrying out the experiments tabulated in Table I, specific details relating to the following topics were taken into consideration: cells employed; electroporation conditions; determination of percent of cells porated; and determination of cells surviving electroporation. Details relating to these topics follow.

Cells

CHO-K1 cells (ATCC) were maintained in complete medium ($CO_2$ Independent medium (Gibco) plus 10% heat inactivated fetal calf serum, 2 mM L-glutamine, 100 units/ml penicillin, 100 $\mu$g/ml streptomycin and 0.25 $\mu$g/ml amphotericin B). Cells were grown in flat bottom T-150 flasks. For suspension cultures, cells were scrapped from T-150 flasks with a cell scraper. The cell suspension was added to a 100 ml spinner flask. Complete medium was added to make a total volume of 100 ml. Spinner flasks were maintained at 37° C. with a stir speed of 80 rpm. Spinner cultures were fed by removing 90% of the cell suspension and replacing the volume with complete medium. For the electroporation, 50 ml of cell suspension was removed from a log phase spinner culture. The cells were counted manually using a hemocytometer. The cells were centrifuged at 400×g for 10 minutes. The cells were resuspended in serum free medium ($CO_2$ Independent medium without supplements) at a concentration of 5 million cells per ml.

Electroporation

A cell suspension volume of 250 μl was added to a sterile, disposable electroporation cuvette (Bio-Rad) with a 2 mm electrode gap. If indicated, 50 μl of either 1% Trypan blue solution (Sigma) or a solution containing 10 μg of plasmid DNA was added to the cuvette. The cuvette was added to a homemade cuvette holder. The pulser and computer control for the electroporation were those described in this patent. The pulser was turned on and the voltage was set. The pulse train was programmed into the attached lap top computer and the pulse train executed by computer control.

Determination of Percent of Cells Porated

Fifty microliters of 1% Trypan blue dye solution (2.4 gm of 44% trypan blue dye added to 100 ml distilled water) was added to the 250 μl of cell suspension in the electroporatiion cuvette. Before applying the high voltage pulses, a 10 μl sample was taken to determine the percent of cells that take up dye (dead cells) prior to electroporation. The pulses were applied to the cells as programmed. After electroporation, a 10 μl sample was taken to determine the percent of cells electroporated. The cells were counted manually on a hemocytometer. Blue cells were counted as positive and clear cells negative. Actual electroporation was calculated by subtracting background from both positive and negative counts.

Determination of Cells Surviving Electroporation

Cells surviving electroporation were determined by the percent of cells able to attach to a tissue culture plate. A 24 well plate was prepared for the assay by adding 1 ml of complete medium to each well. Cells were added to the electroporation cuvette as described. A 10 μl (20 μl in some experiments) sample of cells was removed from the cuvette and placed into a well of the 24 well plate. Cells were rocked to evenly spread them across the plate. After the pulse session was applied, an equal sample was taken from the cuvette and placed into a different, adjacent well of the 24 well plate. Cells were cultured overnight at 37° C. The next day, cells were washed in PBS and fixed in 10% buffered formalin for 1 hour. Cells were washed with PBS then distilled water. Cells were stained with 1% Crystal Violet in distilled water by adding 400 μl dye to each well. The cells were incubated for 5 min then washed with distilled water until no dye was eluted from the plate. The cells were air dried until reading of the plate. One ml of 70 % alcohol was added to each well and incubated for 5 min. The optical density of the alcohol-dye mixture was measured at 592 nM with an alcohol blank. Percent live cells was calculated as OD of sample after electroporation divided by OD of the sample before electroporation.

TABLE I

Comparison of percent poration and percent of cells surviving poration. In accordance with the invention, multiple sets of pulses having a 10 μs pulse width and having a 400 volt pulse amplitude were preceded by longer duration single pulses of either 40 μs plus 20 μs (for Group A) or 20 μs alone (for Group B). A prior art set of pulses is provided by Group C.

| Number of 10 μs Pulses[1,2] | Group A[3] | | Group B[4] (PRIOR ART) | | Group C[5] | |
|---|---|---|---|---|---|---|
| | % porated | % live | % porated | % live | % porated | % live |
| 0 | 25.51 | 81.98 | 16.45 | 90.97 | ND | ND |
| 1 | 55.62 | 87.91 | 15.72 | 99.45 | 5.25 | 94.05 |
| 2 | 55.62 | 86.94 | 12.11 | 92.11 | 12.03 | 87.75 |
| 4 | 81.51 | 85.84 | 29.88 | 88.46 | 28.48 | 77.2 |
| 8 | 88.29 | 95.14 | 85.08 | 94.34 | 70.52 | 77.36 |
| 16 | 96.31 | 76.99 | 98 | 80.01 | 83.96 | 70.59 |

[1]All pulse voltages were 400 volts producing an electric field of 2000 volts/cm.
[2]Pulse intervals were 0.1 second.
[3]Group A. In accordance with the invention, pulse trains of 10μ seconds were preceded by a single pulse of 40 μs and a single pulse of 20 μs.
[4]Group B. In accordance with the invention, pulse trains of 10 μs were preceded by a single pulse of 20 μs.
[5]Group C. As presented in the prior art, pulse trains of 10 μs were delivered without preceding pulses.

In interpreting the results of the experiments tabulated in Table I, it is recalled that Group C data represent a prior art pulse train of pulses having a constant pulse amplitude of 400 volts, having a constant pulse interval of 0.1 seconds, and having a constant pulse width of 10 microsecs.

The data for Group A represent a pulse train in accordance with the invention in which pulses have three different pulse widths. For the pulses for Group A, the pulses have a constant pulse amplitude and a constant pulse interval.

The data for Group B represent a pulse train in accordance with the invention in which pulses have two different pulse widths. For the pulse for Group B, the pulses have a constant pulse amplitude and a constant pulse interval.

It is noted that, generally, the larger the number of pulses, the larger the percentage of porated cells. This is true for both the prior art pulse train (Group C) and the two pulse trains of the invention (Groups A and B). The maximum percent poration for the prior art pulse train is 71.9%. However, in sharp contrast, the maximum percent poration for Group A pulse trains of the invention is 95.8%. The maximum percent poration for Group B pulse trains of the invention is 96.0%. Clearly, with the invention, the percent poration exceeds the prior art percent poration.

With respect to viability, the average percent live for Group C modestly exceeds the average percent live for either Group A or Group B. However, the large disparities in percent poration offset the viability differences.

To derive further meaning from the data present in Table I, Table II has been prepared. Table II relates to the fact that success in electroporation depends upon both the number of cells that are porated and the number of cells that remain alive. In Table II, for each group of data, a product has been obtained by multiplying the value of %porated by its corresponding value of %live. Such products provide a composite number that represents both the number of porated cells and the number of cells which survive the electroporation process. Such a composite number is more representative of the efficacy of electroporation that either %poration or %live alone.

TABLE II

For each of the data in Groups A, B, and C, respectively, in Table I, multiply % porated × % live. This product gives a composite figure for the overall electroporation efficiency taking into account both the extent of poration and the viability of the cells.

| Number of 10 $\mu s$ Pulses | Group A (% porated × % live) | Group B (% porated × % live) | Group C (% porated × % live) |
| --- | --- | --- | --- |
| 0 | 2091 | 1493 | — |
| 1 | 3218 | 1563 | 494 |
| 2 | 4836 | 1115 | 1056 |
| 4 | 6997 | 2643 | 2199 |
| 8 | 8400 | 8026 | 5455 |
| 16 | 7415 | 7841 | 5927 |

Clearly, the products for each of Groups A and B (the invention) exceed the corresponding product for Group C (prior art). Clearly, then, the overall electroporation efficiency, taking into account both the extent of poration and the viability of the cells, is greater with pulse trains of the invention than with the prior art.

It is apparent from the above that the present invention accomplishes all of the objects set forth by providing a method of treating materials with pulsed electrical fields provides a process for application of a series of electrical pulses to living cells wherein the electrical pulses produce reduced cell lethality. With the invention, a method of treating materials with pulsed electrical fields provides an operator of electrical pulse equipment a process for maximum operator control of an applied pulse series. With the invention, a method of treating materials with pulsed electrical fields is provided which provide a process for changing pulse width during a series of electrical pulses. With the invention, a method of treating materials with pulsed electrical fields is provided which provide a process for changing pulse voltage during a series of electrical pulses. With the invention, a method of treating materials with pulsed electrical fields provides a machine for control of the process. With the invention, a method of treating materials with pulsed electrical fields provides a pulse protocol that sustains induced pores formed in electroporation. With the invention, a method of treating materials with pulsed electrical fields provides a pulse protocol which provides three or more pulses to allow more time for materials to enter cells undergoing electroporation. With the invention, a method of treating materials with pulsed electrical fields provides an electrical way to improve cell survival and transfection efficiency. With the invention, a method of treating materials with pulsed electrical fields provides a method of electroporation in which maximum transformation efficiency is achieved when greater than 40% of cells survive the pulse effecting electroporation.

While the present invention has been described in connection with the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:

1. An electrical control circuit for connection between a high voltage power supply and a high voltage switch assembly and connection across a capacitor and to a ground for controlling discharge from the capacitor through the high voltage switch assembly, comprising:

a discharge resistor having a first resistor connection and a second resistor connection, wherein said first resistor connection is connected to a high voltage terminal, a relay which includes a relay input and a normally closed switch having a first switch connection and a second switch connection, wherein said second resistor connection of said discharge resistor is connected to said first switch connection, and wherein said second switch connection is connected to the ground, a voltage divider assembly having a first divider connection connected to the high voltage terminal, a second divider connection connected to the ground, and a third divider connection located between said first and second divider connections, and a voltage comparator assembly which includes a first comparator input connection, a second comparator input connection, and a comparator output connection, wherein said comparator output connection is connected to said relay input, wherein said first comparator input connection is connected to said third divider connection, wherein said first comparator input connection is further connected to a power supply voltage monitoring output, and wherein said second comparator input is connected to a power supply voltage programmed output.

* * * * *